(12) United States Patent
Lin et al.

(10) Patent No.: US 9,005,440 B2
(45) Date of Patent: Apr. 14, 2015

(54) HEMODIALYSIS AND PERITONEAL DIALYSIS SYSTEMS HAVING ELECTRODIALYSIS AND ELECTRODEIONIZATION CAPABILITIES

(71) Applicants: Baxter International Inc., Deerfield, IL (US); Baxter Healthcare S.A., Glattpark (Opfikon) (CH)

(72) Inventors: Rongsheng Lin, Buffalo Grove, IL (US); Yuanpang Samuel Ding, Libertyville, IL (US); James M. White, Grayslake, IL (US); Ye Chen, Buffalo Grove, IL (US); Ying-Cheng Lo, Green Oak, IL (US); Joshua Miller, Wilmette, IL (US); Justin Rohde, Des Plaines, IL (US)

(73) Assignees: Baxter International Inc., Deerfield, IL (US); Baxter Healthcare S.A., Glattpark (Opfikon) (CH)

(*) Notice: Subject to any disclaimer, the term of this patent is extended or adjusted under 35 U.S.C. 154(b) by 7 days.

(21) Appl. No.: 13/796,799

(22) Filed: Mar. 12, 2013

(65) Prior Publication Data

US 2013/0186759 A1 Jul. 25, 2013

Related U.S. Application Data

(63) Continuation-in-part of application No. 12/718,609, filed on Mar. 5, 2010.

(60) Provisional application No. 61/158,101, filed on Mar. 6, 2009.

(51) Int. Cl.
*A61M 1/16* (2006.01)
*A61M 1/28* (2006.01)
(Continued)

(52) U.S. Cl.
CPC ............ *A61M 1/1696* (2013.01); *A61M 1/28* (2013.01); *A61M 1/287* (2013.01); *B01D 61/243* (2013.01); *B01D 61/44* (2013.01); *B01D 61/58* (2013.01); *A61M 1/1674* (2014.02)

(58) Field of Classification Search
CPC . A61M 1/1674; A61M 1/1696; A61M 1/287; A61M 1/28; B01D 61/243; B01D 61/44; B01D 61/58
USPC ........... 210/748.1, 748.11, 195.1, 195.2, 200, 210/252, 263, 294, 295, 321.6, 501, 502.1; 204/520, 535, 630, 632, 628, 637, 540, 204/536, 539; 604/6.08, 6.09, 28, 29
See application file for complete search history.

(56) References Cited

U.S. PATENT DOCUMENTS

| 3,617,545 | A | 11/1971 | DuBois et al. |
| 2008/0164209 | A1 | 7/2008 | Zacerkowny et al. |
| 2010/0224492 | A1 | 9/2010 | Ding et al. |
| 2012/0273354 | A1 | 11/2012 | Orhan et al. |
| 2013/0186759 | A1 | 7/2013 | Lin et al. |

FOREIGN PATENT DOCUMENTS

WO  WO2010024963  3/2010

OTHER PUBLICATIONS

Manns et al., The acu-menTM: A new device for continuous renal replacement therapy in actue renal failure, Kidney International, 1998, pp. 268-274, vol. 54.

(Continued)

*Primary Examiner* — John Kim
(74) *Attorney, Agent, or Firm* — K&L Gates LLP

(57) ABSTRACT

Systems and methods for hemodialysis or peritoneal dialysis having integrated electrodialysis and electrodeionization capabilities are provided. In an embodiment, the dialysis system includes a carbon source, a urease source, an ED/EDI unit. The carbon source, urease source, and/or the ED/EDI unit can be in the form of removable cartridges.

15 Claims, 15 Drawing Sheets

(51) Int. Cl.
*A61M 1/36* (2006.01)
*B01D 61/26* (2006.01)
*B01D 61/44* (2006.01)
*B01D 61/46* (2006.01)
*B01D 61/58* (2006.01)
*B01D 61/24* (2006.01)

(56) References Cited

OTHER PUBLICATIONS

International Search Report dated May 22, 2014 corresponding to International Application No. PCT/US2014/016376.
International Written Opinion dated May 22, 2014 corresponding to International Application No. PCT/US2014/016376.

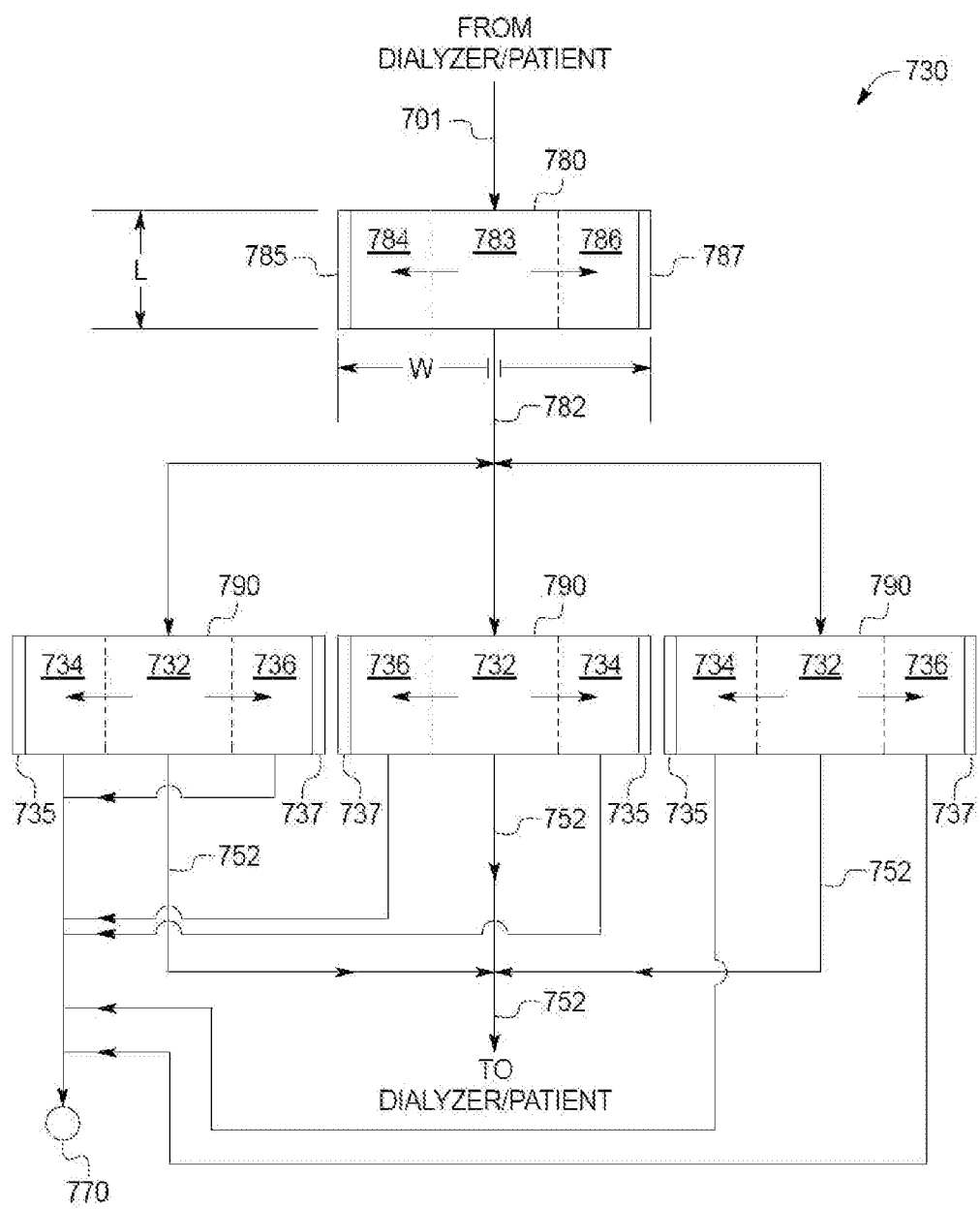

HEMODIALYSIS AND PERITONEAL DIALYSIS SYSTEMS HAVING ELECTRODIALYSIS AND ELECTRODEIONIZATION CAPABILITIES

PRIORITY CLAIM

This application claims priority to and the benefit as a continuation-in-part of U.S. patent application Ser. No. 12/718,609, filed Mar. 5, 2010, which in turn claims priority to U.S. Provisional Patent Application No. 61/158,101, filed Mar. 6, 2009, the entire contents of each of which are expressly incorporated herein by reference.

BACKGROUND

The present disclosure generally relates to dialysis systems. More specifically, the present disclosure relates to systems and methods for hemodialysis or peritoneal dialysis that recycle used dialysate through an electrodialysis- and electrodeionization-based regeneration system. These systems can perform high volume dialysis treatments without using large volumes of fresh dialysis fluid.

In both hemodialysis ("HD") and peritoneal dialysis ("PD"), two general classes of dialysis systems currently exist. The first class uses fresh fluid (e.g., from a solution bag or some sort of water purification system) to generate dialysis fluid that is used to dialyze the individual. The second class uses "sorbent" technology to remove uremic toxins from waste dialysate. Therapeutic agents such as ions and/or glucose can be injected into the treated dialysate, which is used to continue the dialysis of the individual. The main advantage of the sorbent based approach is that very low volumes of fluid are required to achieve high volume dialysis treatments.

Disadvantages of sorbent systems include their high cost, disposability, and concerns regarding the purity of the recycled solution, as many ions remain in the fluid after treatment and verification of purity is technically challenging to perform. For example, sorbents can have high cartridge costs, insufficient removal of all of the tap water impurities, and insufficient removal of all of the uremic toxins in the used dialysate (e.g., sulfate). In addition, possible chemicals may be released or leached from the sorbent cartridge (e.g., zirconium). There may also be potential issues with pH and sodium balance.

SUMMARY

The present disclosure relates to systems and methods for hemodialysis, hemofiltration, hemodiafiltration or peritoneal dialysis having integrated electrodialysis ("ED") and electrodeionization ("EDI") capabilities. The ED/EDI systems and methods can further be utilized in portable dialysis devices such as wearable artificial kidneys. In a general embodiment, the dialysis system includes a carbon source, a urease source, and an ED/EDI unit. The carbon source, urease source, and/or the ED/EDI unit can be in the form of removable cartridges. The ED/EDI approach maintains the advantage of low fluid use in a sorbent system, but addresses the key shortcomings of the sorbent system. The ED/EDI technology is re-usable over very long periods of time (e.g., 5 to 7 years) thereby reducing cost, and essentially removes all ionic contaminants from the waste dialysate (not just selective ions), resulting in verifiably pure recycled solution.

In another embodiment, the disclosure provides a method of performing hemodialysis. The method comprises passing a spent dialysis fluid from a dialyzer through a carbon source, a urease source and an ED/EDI unit to produce a clean dialysis fluid, and passing the clean dialysis fluid through the dialyzer. The clean dialysis fluid can pass through an ion exchange unit before passing through the dialyzer. In addition, one or more dialysis components can be added to the clean dialysis fluid before the clean dialysis fluid passes through the dialyzer.

In an alternative embodiment, the present disclosure provides a method of performing peritoneal dialysis. The method comprises passing a spent dialysis fluid from an individual through a carbon source, a urease source and an ED/EDI unit to produce a clean dialysis fluid, and returning the clean dialysis fluid to the individual. The clean dialysis fluid can pass through an ion exchange unit before returning to the patient. One or more dialysis components can be added to the clean dialysis fluid before returning to the individual. The clean dialysis fluid can also pass through a filter or an ultraviolet bactericidal light returning to the patient.

In yet another embodiment, the present disclosure provides a method of performing dialysis. The method comprises passing a spent dialysis fluid through a dialysis compartment of a dialyzer including an ion-rejection membrane that allows the passage of negatively charged ions and nonionic species but restricts the passage of positively charged ions. The ion-rejection membrane separates the dialysis compartment from a dialysate compartment of the dialyzer. The method further comprises passing used dialysis fluid generated from the dialysate compartment of the dialyzer through a carbon source, a urease source and an ED/EDI unit to produce a clean dialysis fluid. A source containing any desired negative ions is then added to the clean dialysis fluid. The clean dialysis fluid passes through the dialysate compartment of the dialyzer.

In an alternative embodiment, the ion-rejection membrane allows the passage of positively charged ions and nonionic species but restricts the passage of negatively charged ions. In this regard, a source containing any desired positive ions is then added to the clean dialysis fluid.

An advantage of the present disclosure is to provide an improved blood treatment, e.g., hemodialysis system.

Another advantage of the present disclosure is to provide an improved peritoneal dialysis system.

Yet another advantage of the present disclosure is to provide a dialysis system that has a high purity of recycled dialysis fluid.

Still another advantage of the present disclosure a dialysis system having low operating costs.

Additional features and advantages are described herein, and will be apparent from, the following Detailed Description and the figures.

BRIEF DESCRIPTION OF THE FIGURES

FIG. 17A is a schematic illustration of one embodiment of a combination ED/EDI unit including commercially available ED unit and three commercially available EDI units.

DETAILED DESCRIPTION

Figure 1:
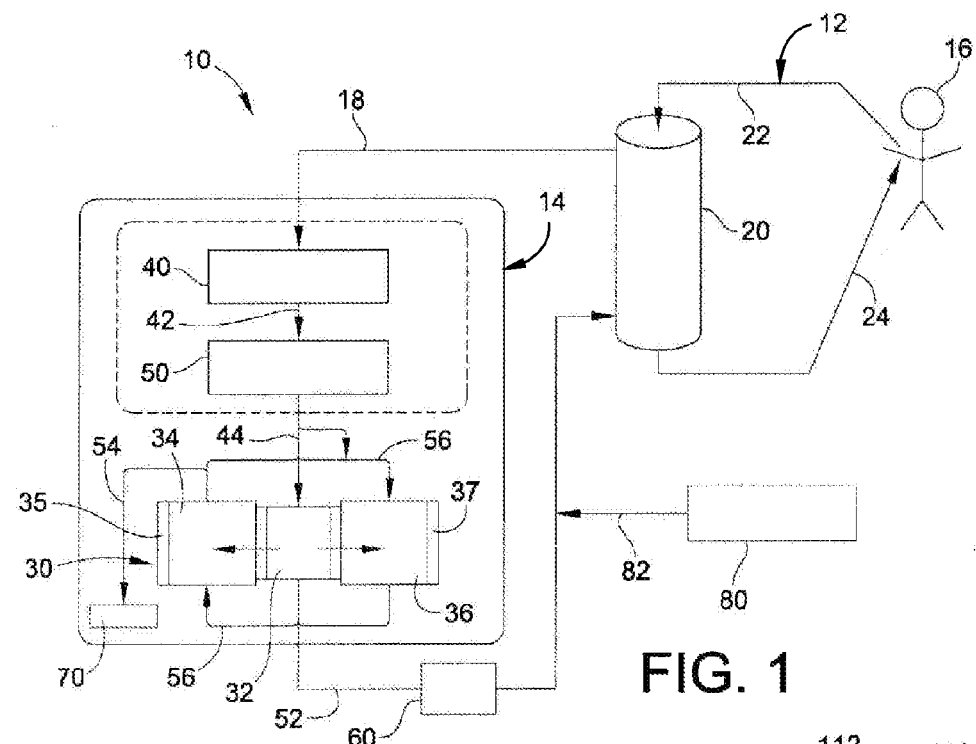
FIG. 1 illustrates a schematic of a dialysis fluid recycling system for hemodialysis in an embodiment of the present disclosure.

The present disclosure relates to systems and methods for hemodialysis or peritoneal dialysis having integrated electrodialysis ("ED") and electrodionization ("EDI") capabilities. In alternative embodiments, the ED/EDI systems and methods can be utilized and implemented in various hemodialysis and peritoneal dialysis technologies. Such dialysis systems are described in U.S. Pat. Nos. 5,244,568, 5,350,357, 5,662,806, 6,592,542 and 7,318,892, which are incorporated herein by reference. The ED/EDI systems and methods can further be utilized in portable dialysis devices such as, for example, wearable artificial kidneys in which an individual may move freely during dialysis. Portable dialysis devices are described in U.S. Pat. Nos. 6,196,992, 5,873,853 and 5,984,891, which are incorporated herein by reference. The ED/EDI systems and methods can be used in medical centers and be implemented with on-site or at-home dialysis treatments.

It should be appreciated that the EDI components of the ED/EDI units discussed herein differ from electrodialyzers (e.g., ED components). There are major differences between electrodialysis and EDI. An electrodialyzer is used to remove electrolytes from an aqueous feed solution introduced into a diluate chamber. An example of an electrolyte is NaCl. However, the level of electrolyte removal is not allowed to go below a certain limit. If one goes to a lower limit with very few electrolyte-based ions left in the solution, water splitting occur (also known as "electrolysis"), and a considerable amount of energy is wasted in splitting the water. This water splitting is needed for the current to flow between the electrodes maintained in the electrodialysis stack. The proton and the hydroxyl ion resulting from the water splitting will carry the current. It is to be avoided for a variety of reasons.

An electrodeionizer is an electrodialyzer in which the diluate channel into which the feed solution is introduced is filled with a bed of mixed ion exchange resin beads. At the top of the channel where the feed solution is introduced, the electrolytes present in the feed solution carry the current. Even though the ion exchange resin beads are there, they do not serve much of a deionization function. The mixed ion exchange resin beads in the electrodeionizer enhance the efficiency of removing the electrolytes from the dialysate solution as well as alleviate the effects of water splitting as a result of little to no electrolytes remaining in the solution further down the channel.

For each of the embodiments discussed herein, the ED and EDI units, whether integrated or separate, can be made of metal, plastic, or some combination thereof. If plastic, the plastic is a medical grade plastic, such as polyvinyl chloride ("PVC)". If metal, the ED and EDI units can be stainless steel. Regardless of material, the ED and EDI units can be reused or be single use. For example, a metal version of the ED and EDI units can be hot water or steam disinfected after a treatment and be reused, say for another hemodialysis or blood treatment. Plastic and hybrid metal/plastic units can also be disinfected for reuse. In another example, a plastic version of the ED and EDI units can be used a single time, e.g., for peritoneal dialysis, and then discarded.

Systems of the Present Disclosure

In a general embodiment, a dialysis fluid recycling system 10 for hemodialysis is illustrated in FIG. 1. As shown in FIG. 1, a circuit 12 represents a standard blood circuit for a hemodialysis machine. Circuit 12 cycles blood from an individual 16 via flow path 22 through a dialyzer 20 and returns it to the individual's body via flow path 24. Dialyzer 20 can include a dialysate compartment and a blood compartment separated by a suitable membrane. A circuit 14 includes an EDI unit or module 30 in dialysis fluid recycling system 10. Module 30 can be constructed and used once or reused as described above. Circuit 14 can also include a carbon source 40 and a urease source 50 connected to carbon source 40 via flow path 42. Carbon source 40, urease source 50, and/or EDI unit 30 can be in the form of one or more removable cartridge, such as part of a disposable or reusable pumping and/or valving cartridge.

EDI unit 30 can include a central chamber 32, an anion chamber 34 having an anode 35, and a cation chamber 36 having a cathode 37. As fluid exiting urease source 50 flows to central chamber 32 via flow path 44, a potential difference between anode 35 and cathode 37 causes the electrolytes in the fluid in central chamber 32 to flow into anion chamber 34 and cation chamber 36. Specifically, negatively charged ions flow into anion chamber 34 while positively charged ions flow into cation chamber 36 where they are subsequently removed. The treated fluid that passes through EDI unit 30 exits as part of a treated fluid stream via flow path 52. A waste fluid stream filled with electrolytes exits via flow path 54 that can lead to a drain 70.

EDI unit 30 can also be modified so that a suitable quantity of fluid can be recirculated around EDI unit 30 via flow path 56. This reduces the amount of fluid flowing through EDI unit 30 that would end up as part of the waste fluid stream. As a result, a higher quantity of fluid exits as the treated fluid stream as compared to the quantity of treated fluid from an EDI unit without recirculation.

During operation, after priming system 10 with an appropriate amount of fluid (in this case, priming fluid can be any of, dialysis fluid, sterile bagged water, tap water in its raw form, tap water purified through standard means such as deionization and/or reverse osmosis, or a combination therein), the dialysis solution is recirculated through circuit 14 via flow path 18 in the direction indicated. Used dialysis fluid leaves dialyzer 20 saturated with uremic toxins, as well as normal dialysis fluid components such as dextrose and ions (e.g., sodium, calcium, magnesium, etc.). The organic toxins of the fluid, as well as the lactate or bicarbonate buffer of the solution, are then removed from the fluid through adsorption onto a carbon surface (e.g. activated carbon or other appropriate organic neutralizing surface) of carbon source 40.

Urea, which is not well removed by carbon, is then exposed to urease source 50. Urease is an enzymatic catalyst which facilitates the breakdown of urea into ammonium and ammonia (e.g., depending on pH). Urease source 50 can be immobilized on any suitable surface that allows the passage of a liquid or be a membrane impregnated with cross-linked unease enzyme crystals.

The pKa of ammonium ion is 9.25. For efficient removal, the pH needs to be below neutral. At lower pH's, a greater portion of ammonia will be in ionized form. Passing it through an optional cation exchanger will help lower the pH and have better removal of ammonia. Removal of the ammonium in can also be accomplished within EDI unit 20.

After the fluid has passed through urease source 50, all organic contaminants will have been adsorbed or broken down into ionic contaminants before entering EDI unit 30. In EDI unit 30, ions are removed from the fluid through electromagnetic facilitated transport through cation and anion selective membranes. The fluid that exits EDI unit 30, in contrast to currently existing sorbent systems, contains very few ions, e.g., with nominal fluid resistivity approaching or in excess of 5 MΩ·cm. In this regard, EDI unit 30 can render the zirconium phosphate layer, zirconium bicarbonate layer and/or ion exchange layer typically used for ammonium/ion removal unnecessary.

After EDI unit 30, ions and/or fluids can be replaced in the clean fluid stream through the addition of one or more concentrated dialysis components from a concentrate or fluid metering source 80 via flow path 82. The concentrated dialysis components can include one or more osmotic agents (e.g., dextrose, icodextrin, glucose polymers, glucose polymer derivatives, amino acids), buffers (e.g., lactate, bicarbonate) and electrolytes (e.g. sodium, potassium, calcium, magnesium) from a small fluid source. After this addition, the fluid is compositionally equivalent to fresh dialysis solution and can be used to remove additional uremic toxins from the individual's blood stream.

To further realize the benefits of EDI over existing sorbent systems, EDI unit 30 would not be expected to be replaced over the foreseeable lifetime of the hemodialysis systems/devices. Carbon source 40 and urease source 50 can be replaced at some determined interval, but these are much lower cost components than sorbent cartridges and do not negatively impact the economic benefits of the system. Alternatively, EDI unit 30 can be provided in the form of a removable or disposable cartridge, such as part of a disposable or reusable pumping and/or valving cassette.

In an embodiment shown in FIG. 1, additions can be made to enhance the functionality and/or safety of the system. For example, biological purity of system 10 can be assured through replacement of circuits 12 and 14 after each treatment, along with dialyzer 20. However, circuits 12 and 14 can also be re-used for multiple treatments if suitable disinfection and sanitization methods were undertaken. These can include all currently accepted methods, such as heat sanitization, chemical sanitization (including ozonation), addition of ultraviolet ("UV") bactericidal lights, and the addition of additional dialyzers and/or ultrafilters in the system with a pore size appropriate for the removal of bacterial and sub-bacterial contaminants.

The monitoring of system 10 can be enhanced through the inclusion of an optional ammonia sensor in the loop after EDI unit 30 to ensure that all ammonia has been removed. Because fluid of resistance approaching 5 MΩ·cm can be made after passing through EDI unit 30, an optional conductivity sensor may be used to assure there is no ammonia versus the traditional approach of using an ammonia sensor. Finally, one or more optional ion exchanger unit 60 that have low cost and/or high capacity can be used to supplement EDI unit 30 to improve its performance or reduce its necessary size. These optional ion exchangers can include a phosphate removal exchanger with a bicarbonate counter ion to enhance phosphate removal or a cation exchanger that helps to remove any remaining ammonia.

The dialyzers in any embodiments of the present disclosure can include an ion-rejection membrane that allows the passage of negatively charged ions and nonionic species but restricts the passage of positively charged ions. Alternatively, the dialyzers in any embodiments of the present disclosure can include an ion-rejection membrane that allows the passage of positively charged ions and nonionic species but restricts the passage of negatively charged ions.

Figure 2:
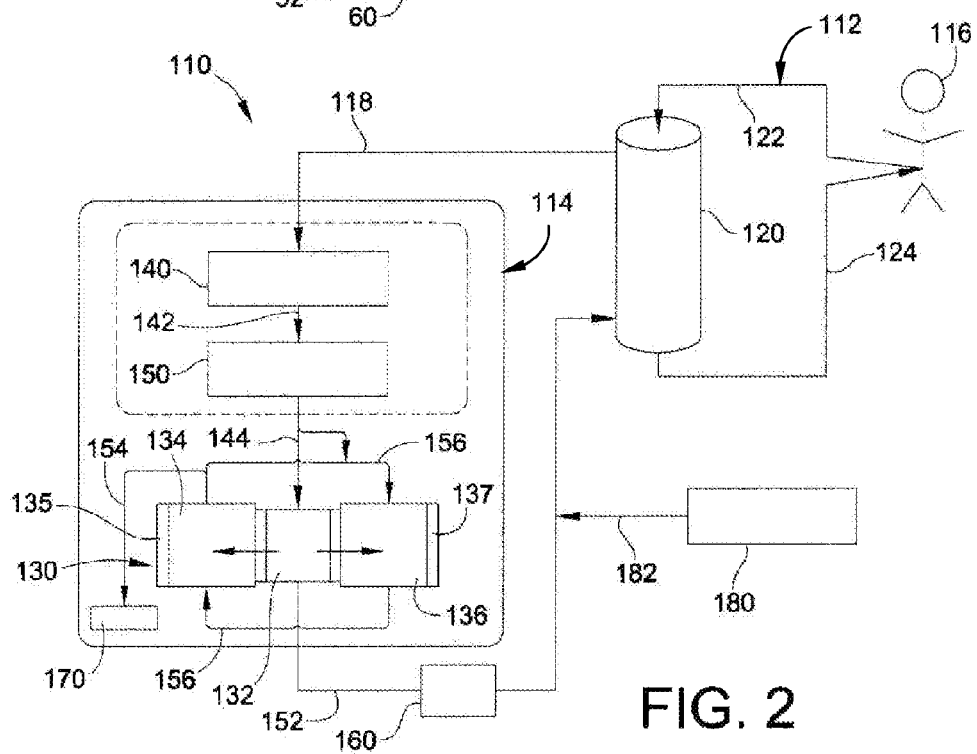
FIG. 2 illustrates a schematic of a dialysis fluid recycling system for peritoneal dialysis in an embodiment of the present disclosure.

In another embodiment, a dialysis fluid recycling system 110 for peritoneal dialysis is illustrated in FIG. 2. As shown in FIG. 2, a circuit 112 cycles spent dialysis fluid from an individual 116 via flow path 122 through a dialyzer 120 and returns it to the individual's body via flow path 124. Dialyzer 120 can include a dialysate compartment and a peritoneal dialysis fluid compartment separated by a suitable membrane. A circuit 114 includes an EDI unit 130 in the dialysis fluid recycling system. EDI unit 130 can be constructed to be reused or used once as described above. Fluid from dialyzer 120 transfers to circuit 114 via flow path 118.

Circuit 114 can also include a carbon source 140 and a urease source 150 connected to carbon source 140 via flow path 142. Circuit 114 can further include an optional ion exchange unit 160 in fluid connection with EDI unit 130 via flow path 152. Flow path 152 can lead directly back to dialyzer 120. Carbon source 140, urease source 150, ion exchange unit 160, and/or EDI unit 130 can be in the form of one or more removable cartridge, such as part of a disposable or reusable pumping and/or valving cassette.

EDI unit 130 can include a central chamber 132, an anion chamber 134 having an anode 135, and a cation chamber 136 having a cathode 137. As fluid flows through central chamber 132 via flow path 144, a potential difference between anode 135 and cathode 137 causes the electrolytes in the fluid in central chamber to flow into anion chamber 134 and cation chamber 136. The treated fluid that passes through EDI unit 130 exits as part of a treated fluid stream 152 that leads back to dialyzer 120. A waste fluid stream filled with electrolytes exits via flow path 54 that leads to a drain 170.

EDI unit 130 can also be modified so that a suitable quantity of fluid can be recirculated around EDI unit 130 via flow path 156. This reduces the amount of fluid flowing through EDI unit 130 that would end up as part of the waste fluid stream.

System 110 is nearly identical to the hemodialysis system 10 of FIG. 1. However, in this embodiment, the solution being passed through circuit 112 represents peritoneal dialysis fluid, rather than individual's 116 own blood. The peritoneal dialysis procedure can be run, for example, in a "continuous flow" mode, where used dialysis fluid exits the individual's peritoneum as new fluid enters it through a dual lumen catheter. The used fluid is passed through dialyzer 120 where uremic toxins are removed and the waste fluid is treated just as it would be in hemodialysis. The composition of a concentrate addition to the fluid stream in flow path 152 from a concentrate or fluid metering source 180 via flow path 182 may be specifically tailored for peritoneal dialysis.

Additions to this type of system, along with those described for the hemodialysis system, can be included to enhance effectiveness or safety of the system. In an embodiment, the typical dialyzer membrane can be replaced with an ion-rejection membrane that allows the passage of negatively charged ions and nonionic species, but restricts the passage of positively charged ions (or vice versa). In this case, the peritoneal dialysis loop that is recirculating to the individual would be cleared of uremic toxins (which are neutrally or negatively charged), but the concentrate addition would not need to include replacement of the positive ions of the dialysis solution, which enhances the efficiency of the system.

Figure 3:
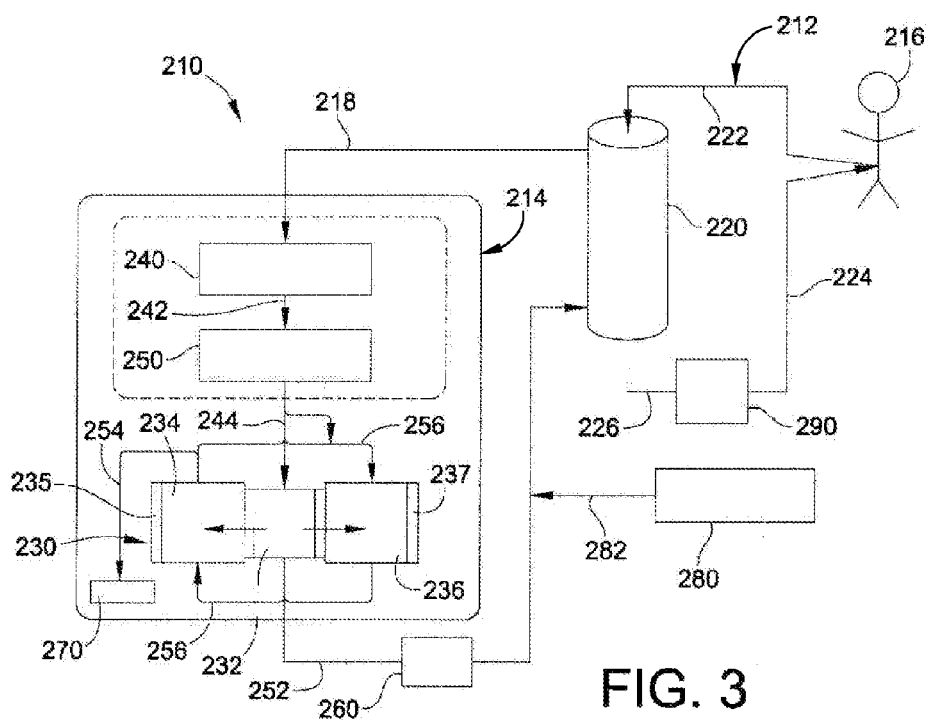
FIG. 3 illustrates a schematic of a dialysis fluid recycling system in another embodiment of the present disclosure.

In an alternative embodiment, a dialysis fluid recycling system 210 for hemodialysis or peritoneal dialysis is illustrated in FIG. 3. As shown in FIG. 3, a circuit 212 cycles fluid from an individual 216 through a dialyzer 220 and returns it to the individual's body. A circuit 214 includes an EDI unit or module 230 in the dialysis fluid recycling system. EDI unit or module 230 can be constructed to be used once or reused as described above.

Circuit 214 can also include a carbon source 240 and a urease source 250 connected to carbon source 240 via flow path 242. Circuit 214 can further include an optional ion exchange unit 260 in fluid connection with EDI unit 230 via flow path 252. Flow path 252 can lead directly back to dialyzer 220. Carbon source 240, urease source 250, ion exchange unit 260, and/or EDI unit 230 can be in the form of one or more removable cartridge, such as part of a disposable or reusable pumping and/or valving cassette.

EDI unit 230 can include a central chamber 232, an anion chamber 234 having an anode 235, and a cation chamber 236 having a cathode 237. As fluid flows through central chamber 232 via flow path 244, a potential difference between anode 235 and cathode 237 causes the electrolytes in the fluid in central chamber to flow into anion chamber 234 and cation chamber 236. The treated fluid that passes through EDI unit 230 exits as part of a treated fluid stream 252. A waste fluid stream filled with electrolytes exits via flow path 254 that leads to a drain 270.

EDI unit 230 can also be modified so that a suitable quantity of fluid can be recirculated around EDI unit 230 via flow path 256. This reduces the amount of fluid flowing through EDI unit 230 that would end up as part of the waste fluid stream.

After leaving EDI unit 230 via flow path 252, one or more dialysis components from a concentrate or fluid metering source 280 via flow path 282 may be specifically tailored for the specific type of dialysis performed. An additional purification or treatment component 290 in the form of a filter or ultraviolet bactericidal light can be added to circuit 212, as shown in FIG. 3. Fluid exiting dialyzer 220 via flow path 226 can be further filtered or subject to a bactericidal light to enhance the bacterial purity of system 210. The treated fluid can then enter individual 216 via flow path 224. Purification component 290 can be especially important to peritoneal dialysis because bacterial contamination is a significant concern for the treatment.

Figure 4:
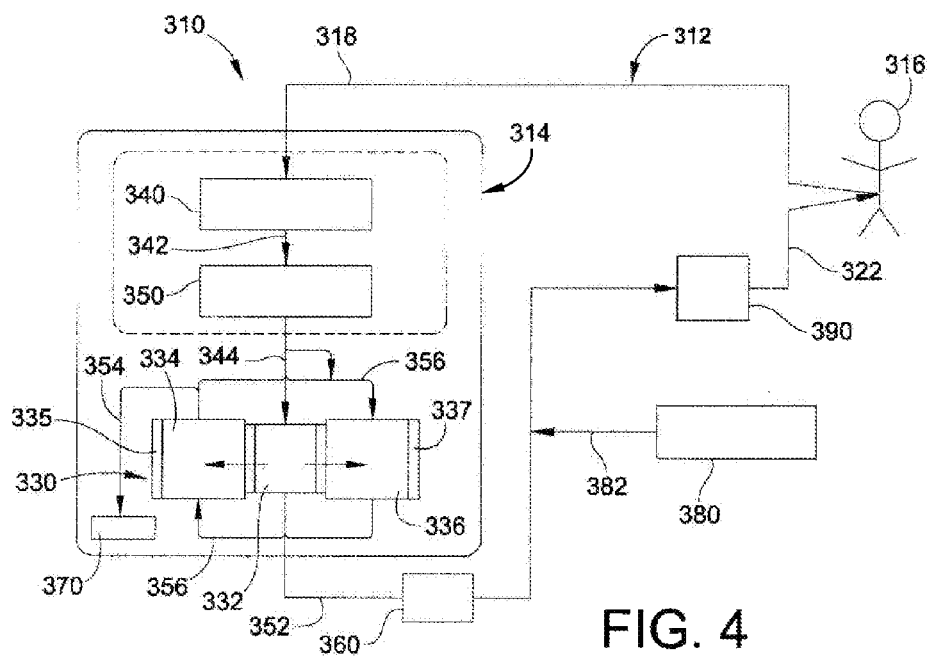
FIG. 4 illustrates a schematic of a dialysis fluid recycling system for peritoneal dialysis in an embodiment of the present disclosure.

In yet another embodiment, a dialysis fluid recycling system 310 for peritoneal dialysis is illustrated in FIG. 4. As shown in FIG. 4, a circuit 312 cycles blood from an individual 316 through a circuit 314. In order to perform the peritoneal dialysis treatment as shown in FIG. 4, flow path 318 of recycling system 310 can be constructed such that spent dialysis fluid from individual 316 is sent directly to recycling system 310 without the need for "dialyzing" the PD fluid. The peritoneal dialysis procedure can be run, for example, in a "continuous flow" mode.

Circuit 314 includes an EDI unit or module 330 in the dialysis fluid recycling system. EDI unit or module 330 can be constructed to be used once or reused as described above. Circuit 314 can also include a carbon source 340 and a urease source 350 connected to carbon source 340 via flow path 342. Circuit 314 can further include an optional ion exchange unit 360 in fluid connection with EDI unit 330 via flow path 352. Flow path 352 can lead directly back to dialyzer 320. Carbon source 340, urease source 350, ion exchange unit 360, and/or EDI unit 330 can be in the form of one or more removable cartridge, such as part of a disposable or reusable pumping and/or valving cartridge.

EDI unit 330 can include a central chamber 332, an anion chamber 334 having an anode 335, and a cation chamber 336 having a cathode 337. As fluid flows through central chamber 332 via flow path 344, a potential difference between anode 335 and cathode 337 causes the electrolytes in the fluid in central chamber to flow into anion chamber 334 and cation chamber 336. The treated fluid that passes through EDI unit 330 exits as part of a treated fluid stream 352. A waste fluid stream filled with electrolytes exits via flow path 354 that leads to a drain 370.

EDI unit 330 can also be modified so that a suitable quantity of fluid can be recirculated around EDI unit 330 via flow path 356. This reduces the amount of fluid flowing through EDI unit 330 that would end up as part of the waste fluid stream.

After leaving EDI unit 330 via flow path 352, one or more dialysis components from a concentrate or fluid metering source 380 via flow path 382 may be specifically tailored for the type of dialysis performed. An additional purifying component 390 such as a filter, UV light, and/or other commonly accepted methods can optionally be used on the inlet line to the individual's 316 peritoneal cavity to prevent bacterial contamination and also on the line from the individual back to system 310 (not shown) to prevent retro-contamination to individual 316. The purified dialysis solution can be provided to individual 316 via flow path 322.

Figure 5:
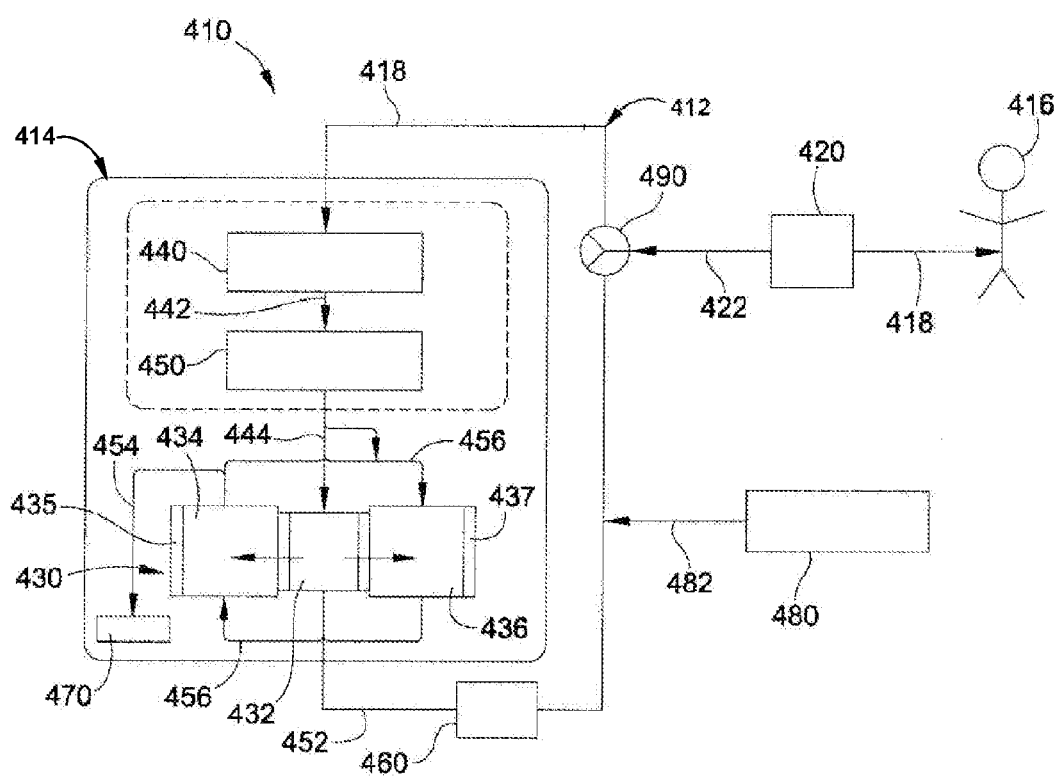
FIG. 5 illustrates a schematic of a dialysis fluid recycling system for peritoneal dialysis in another embodiment of the present disclosure.

In yet another embodiment, a dialysis fluid recycling system 410 for peritoneal dialysis is illustrated in FIG. 5. As shown in FIG. 5, a circuit 412 cycles dialysis fluid from an individual 416 to via flow path 422 to a three way valve 490. From three-way valve 490, the fluid flows to a circuit 414 via flow path 418 where the fluid is recycled. System 410 is designed to operate in a standard peritoneal dialysis therapy mode where fluid is injected, allowed to dwell, then removed from individual 416. Once the dialysis fluid has been purified, the dialysis fluid is then sent back to individual 416 via flow path 418, allowed to dwell, removed, purified, and repeated.

The control of the flow direction can be accomplished with three-way valve 490 as shown in FIG. 5.

Circuit 414 includes an EDI unit 430. EDI unit or module 430 can be constructed to be used once or reused as described above. Circuit 414 can also include a carbon source 440 and a urease source 450 connected to carbon source 440 via flow path 442. Circuit 414 can further include an optional ion exchange unit 460 in fluid connection with EDI unit 430 via flow path 452. Flow path 552 can lead directly back to dialyzer 420. Carbon source 440, urease source 450 and/or ion exchange unit 460 can be in the form of removable cartridges. After leaving EDI unit 430 via flow path 452, one or more dialysis components from a concentrate or fluid metering source 480 via flow path 482 may be specifically tailored for the type of dialysis performed.

EDI unit 430 can include a central chamber 432, an anion chamber 434 having an anode 435, and a cation chamber 436 having a cathode 437. As fluid flows through central chamber 432 via flow path 444, a potential difference between anode 435 and cathode 437 causes the electrolytes in the fluid in central chamber to flow into anion chamber 434 and cation chamber 436. The treated fluid that passes through EDI unit 430 exits as part of a treated fluid stream 452. A waste fluid stream filled with electrolytes exits via flow path 454 that leads to a drain 470.

EDI unit 430 can also be modified so that a suitable quantity of fluid can be recirculated around EDI unit 430 via flow path 456. This reduces the amount of fluid flowing through EDI unit 430 that would end up as part of the waste fluid stream.

Figure 8:
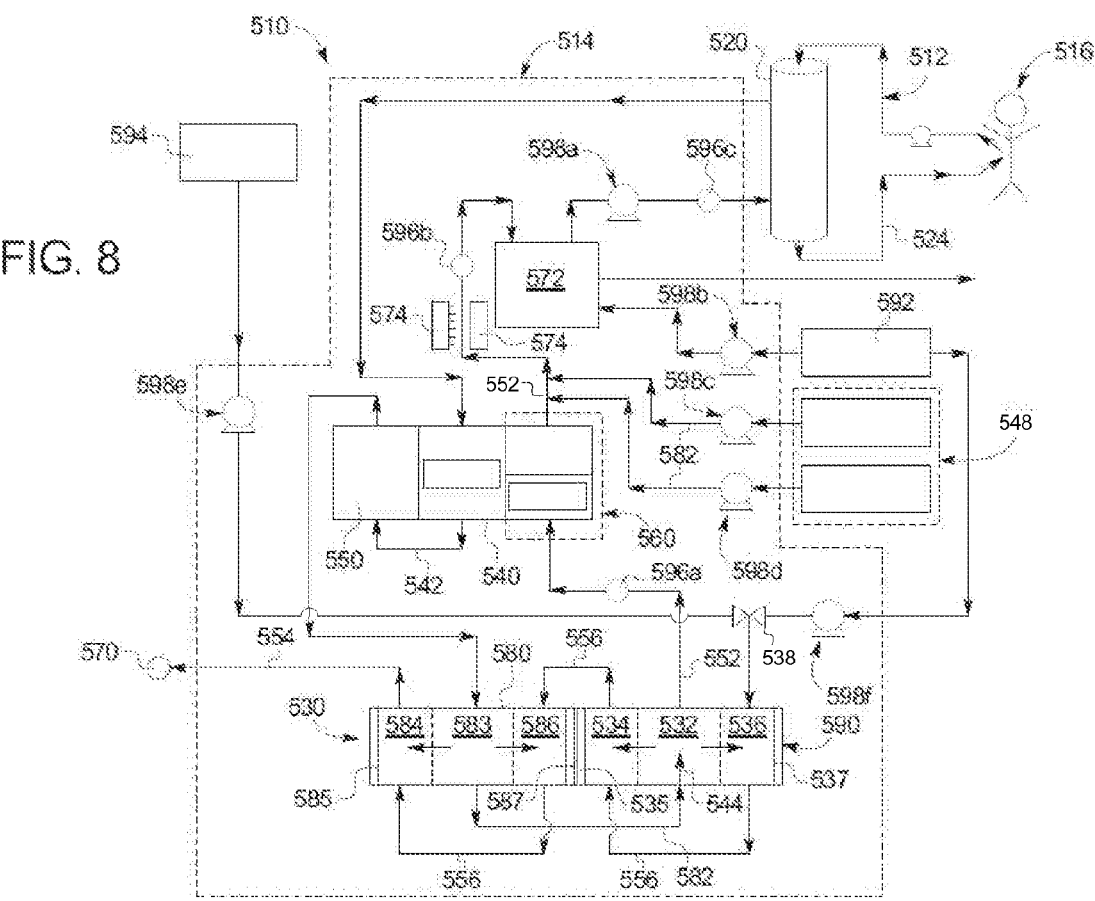
FIG. 8 is a schematic of a dialysis fluid recycling system in another embodiment of the present disclosure.

In still another alternative embodiment, a dialysis fluid system 510 for hemodialysis (or other blood treatment) or peritoneal dialysis, having recycling capabilities, is illustrated in FIG. 8. In this embodiment, the water source for regeneration of dialysate is an ultrapure, sterile or injectable quality water source 592, which is fed via pump 598*f* and associated valves to ED/EDI unit 530. Water source can for example be a water purification machine, such as one set forth in U.S. Patent Publication No. 2011/0197971, entitled, "Water Purification System And Method", filed Apr. 25, 2011, the entire contents of which is incorporated herein by reference and relied upon. In some embodiments, about twelve to eighteen liters of ultrapure or sterile water per dialysis session are provided by sterile water source 592. This twelve to eighteen liters of water is used to replenish fluid pumped or delivered to drain 570.

As shown in FIG. 8, a blood or peritoneal dialysis fluid circuit 512 cycles fluid, e.g., from an individual 516 through a dialyzer 520 and returns the fluid to the individual's body. A dialysis fluid recirculation circuit 514 includes a combination ED/EDI unit or module 530. A peritoneal dialysis application may use dialyzer 520 and separate circuits 512 and 514. Here circuit 512 is sterile, while circuit 514 can be less than sterile due to the separation by the membranes of dialyzer 520. Alternatively, dialyzer 520 is removed and circuits 512 and 514 are merged into one another, eliminating structure and possibly a pump. Here, however, the fluid returning directly to the patient via the recirculation and cleaning loop needs to be sterile or injectable quality. The combination ED/EDI unit 530 includes an ED component 580 in fluid connection with an EDI component 590 via flow path 582. ED/EDI unit or module 530 can be constructed to be used once or reused as described above.

The ED component 580 in the illustrated embodiment includes a central chamber 583, an anion chamber 584 having an anode 585, and a cation chamber 586 having a cathode 587. As spent fluid flows through central chamber 583 via flow path 584, a potential difference between anode 585 and cathode 587 causes the electrolytes in the fluid in central chamber 583 to flow or migrate into anion chamber 584 and cation chamber 586. The treated fluid that passes through the ED component 580 enters the EDI component 590 via flow path 582. A waste fluid stream filled with electrolytes exits ED component 580 via flow path 554 that leads to a drain 570.

The EDI component 590 in the illustrated embodiment includes a central chamber 532, an anion chamber 534 having an anode 535, and a cation chamber 536 having a cathode 537. EDI component 590, and in the illustrated embodiment cation chamber 536 of component 590, is in fluid connection at junction 538 with an acid solution or acid concentrate 594 and sterile water source 592. System 510 includes valves (not illustrated), such as valves operating in conjunction with fluid pumps 598*e* and 598*f*, to selectively deliver acid concentrate and/or ultrapure, sterile or injectable water to EDI component 590. As spent dialysate flows through central chamber 532 via flow path 544, a potential difference between anode 535 and cathode 537 causes the electrolytes in the fluid in central chamber 532 to flow or migrate into anion chamber 534 and cation chamber 536. The treated dialysis fluid that passes through the EDI component 590 exits as part of a treated fluid stream 552.

The ED/EDI unit 530 can also be modified as illustrated so that a suitable quantity of fluid can be recirculated around the ED/EDI unit 530 via flow path 556. In the illustrated embodiment, a separate bypass or recirculation path 536 is provided for both ED component 580 and EDI components 590. Alternatively, a single bypass or recirculation line is provided for the entire ED/EDI unit 530, which extends from anywhere within ED component 580 to anywhere within EDI component 590. Recirculation reduces the amount of fluid flowing through ED/EDI unit 530 that would end up as part of the waste fluid stream discarded to drain 570.

Dialysis fluid circuit 514 can also include a carbon source 540 and a urease source 550 connected to carbon source 540 via flow path 542. Carbon source 540, urease source 550, ion exchange unit 560 (discussed below), and/or ED/EDI unit 530 can be provided in the form of one or more removable cartridges or cassettes, which may or may not also include ED/EDI unit 530. In the illustrated embodiment, fluid exiting dialyzer 520 or the patient is fed first through carbon source 540 and urease source 550 before reaching ED/EDI unit 530. Carbon source 540 and urease source 550 could be located alternately downstream of ED/EDI unit 530.

Recirculation circuit 514 can further include an optional ion exchange unit 560 in fluid connection with ED/EDI unit 530 via flow path 552. Flow path 552 leaving ion exchange unit 560 can lead directly back to dialyzer 520 or to a dialysate reservoir 572, e.g., a bag or rigid container. Pump 598*b* and its associated valves pump and direct ultrapure, sterile or injectable quality water from source 592 into reservoir 572. Pump 598*a* and its associated valves pump and direct the cleaned and replenished dialysis fluid (e.g., from reservoir 572) to dialyzer 520 or HD or PD or directly to patient 516 for PD. Element 572 can alternatively be or additionally include a filter, such as an ultrafilter to further clean the dialysate, e.g., so that the dialysate is close to or at an injectable quality level.

After leaving ED/EDI unit 530 via flow path 552, one or more dialysis components from a concentrate metering source 548 via flow paths 582 may be introduced back into the cleaned dialysis fluid stream for mixing at reservoir 572, e.g., via one or more pump 598*c* and 598*d* and associated valves. The mixing may also include purified water from source 592. The concentrates in general include electrolytes and/or glucose/dextrose and are tailored for the specific type of dialysis performed. An additional purification or treatment component in the form of a filter or ultraviolet bactericidal light 574 can be added to recirculation circuit 514. As is illustrated in FIG. 8, light 570 can be placed in dialysis circuit 514 as shown or blood or peritoneal dialysis treatment fluid can be directly subjected to bactericidal light 574 to enhance the bacterial purity of system 510. The treated fluid (blood or dialysate) can then enter individual 516 via flow path 524.

Circuits of the present disclosure may further include one or more conductivity sensor. Conductivity sensors may be placed at any suitable location along the fluid flow pathway. For example, and referring to the particular embodiment shown in FIG. 8, a conductivity sensor 596a may be placed in fluid connection between EDI component 590 and ion exchange unit 560, such that the conductivity of the dialysis fluid (and therefore the ion content of the fluid) exiting the EDI component 560 can be determined. Further or alternatively, a conductivity sensor 596b can be placed in fluid connection between ion exchange unit 590 and dialysate reservoir 572 (when present) or dialyzer 520. When dialysate reservoir 572 is present, a conductivity sensor 596c may be in fluid connection between dialysate reservoir 572 and dialyzer 520. Thus, in some embodiments, recirculation circuit 514 includes at least two of conductivity sensors 596a, 596b, and 596c. In some embodiments, recirculation circuit 514 includes all three of conductivity sensors 596a, 596b and 596c.

Conductivity sensors 596a to 596c are temperature compensated in one embodiment. The conductivity sensors in essence confirm that salt ions have been removed when desired (e.g., at sensor 596a) and have in turn been added back into solution when desired (e.g., at sensors 596b and 596c). As discussed, system 510 and other systems of the present disclosure may further include one or more fluid pump for transporting spent dialysate, regenerated dialysate, reagent concentrates, water, or other fluids throughout the circuit. In some embodiments, for example the embodiment shown in FIG. 8, plural pumps 598a to 598f are used to transport various fluids. The pumps can be machine actuated fluid pumps. For example, embodiments in which pump dialysate reservoir 572 is used to hold regenerated dialysate, pump 598a feeds regenerated dialysate to dialyzer 520. Ultrapure or sterile water is likewise provided from ultrapure or sterile water source 592 to dialysate reservoir 572 via pump 598b and to EDI component 590 via pump 598f. And as discussed, acid concentrate and bicarbonate are provided from concentrate or fluid metering source 548 via pump 598c and/or 598d. Acid solution from acid source 594 is provided to ED component 580 via pump 598e. Pumps 598a to 598f can be membrane pumps, rotary peristalistic pumps, linear peristalistic pumps, shuttle pumps, or microfluidic pumps, which can be provided in any combination and hybridization to maximize performance and cost. Pumps 598a to 598f can have fluid contacting portions or chambers that are provided as part of a disposable cassette or be tubing portions that operate with tubing actuators.

Figure 9:
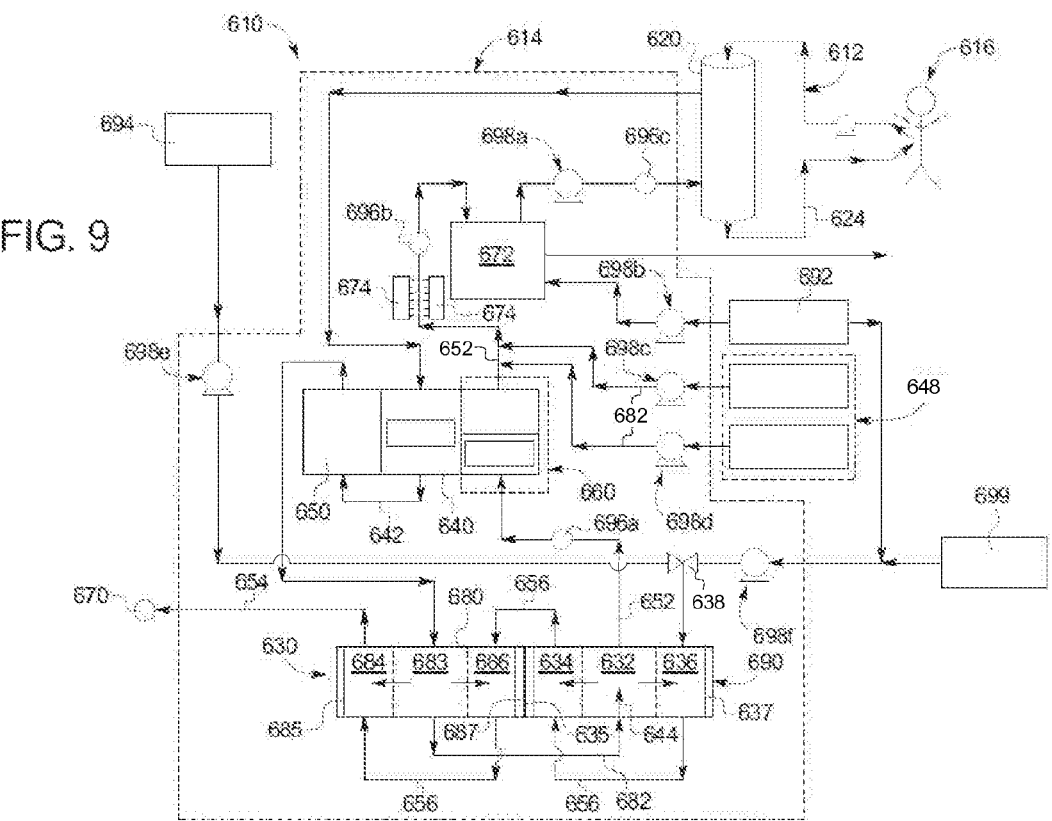
FIG. 9 is a schematic of a dialysis fluid recycling system in a further embodiment of the present disclosure.

Referring generally now to FIG. 9, a dialysis fluid system 610 for hemodialysis or peritoneal dialysis, having recycling capabilities, is shown in which water for regenerating dialysate is provided in part by a purified or sterile water source 692 and in part from tap water source 699. Alternately, tap water 699 is used as the sole source for regeneration water. In some embodiments, about six to twelve liters of ultrapure or sterile water per dialysis session are provided by purified or sterile water source 692 and the balance of water required to regenerate dialysate, e.g., up to eighteen total liters, is provided by tap water source 699. Alternatively, all twelve to eighteen liters of regeneration water is tap water from source 699.

As shown in FIG. 9, system 610 is otherwise very similar to or the same as system 510. For example, a blood or peritoneal dialysis sterile fluid circuit 612 cycles fluid, e.g., blood or sterile peritoneal dialysis fluid, from an individual 616 through a dialyzer 620 and returns the fluid to the individual's body. A recirculation circuit 614 includes a combination ED/EDI unit or module 630 in the dialysis fluid recycling regime. As with system 510, system 610 in a peritoneal dialysis application may provide the recirculation loop as a secondary loop using dialyzer 620 or provide the recirculation loop in a single loop arrangement, eliminating dialyzer 620 and merging circuits 612 and 614. Here, dialysis fluid returning directly to the patient needs to be sterile or of injectable quality. The combination ED/EDI unit 630 includes an ED component 680 in fluid connection with an EDI component 690 via flow path 682. ED/EDI unit or module 630 can be constructed and used once or reused as described above.

As with System 510, ED component 680 can include a central chamber 683, an anion chamber 684 having an anode 685, and a cation chamber 686 having a cathode 687. As fluid flows through central chamber 683 via flow path 684, a potential difference between anode 685 and cathode 687 causes the electrolytes in the fluid in central chamber to flow or migrate into anion chamber 684 and cation chamber 686. The treated fluid that passes through the ED component 680 enters the EDI component 690 via flow path 682. A waste fluid stream filled with electrolytes exits via flow path 654 that leads to a drain 670.

The EDI component 690 can again include a central chamber 632, an anion chamber 634 having an anode 635, and a cation chamber 636 having a cathode 637. EDI component 690 is in fluid connection at junction 638 with an acid solution or acid concentrate 694 and sterile water source 692. As spent dialysate flows through central chamber 632 via flow path 644, a potential difference between anode 635 and cathode 637 causes the electrolytes in the fluid in central chamber to flow or migrate into anion chamber 634 and cation chamber 636. The treated fluid that passes through the EDI component 690 exits as part of a treated fluid stream 652.

The ED/EDI unit 630 can also be modified so that a suitable quantity of fluid can be recirculated around the ED/EDI unit 630 via flow paths 656 or via a single recirculation path 656 connected to both ED component 680 and EDI component 690. Again, recirculation reduces the amount of fluid flowing through ED/EDI unit 630 that would end up as part of the waste fluid stream discarded to drain 670.

Recirculation circuit 614 can also include a carbon source 640 and a urease source 650 connected to carbon source 640 via flow path 642. Circuit 614 can further include an optional ion exchange unit 660 in fluid connection with ED/EDI unit 630 via flow path 652. Flow path 652 can lead directly back to dialyzer 620 or to a dialysate reservoir 672. Carbon source 640, urease source 650, ion exchange unit 660, and/or ED/EDI unit 630 can be in the form of removable cartridges. As with system 510, carbon source 640 and urease source 650 receive spent fluid from dialyzer 620 and feed fluid to ED/EDI unit 630. Carbon source 640 and urease 650 are alternatively downstream of ED/EDI unit 630.

After leaving ED/EDI unit 630 via flow path 652, one or more dialysis components from a concentrate or fluid metering source 648 via flow path 682 may be specifically tailored for the specific type of dialysis performed and mixed with purified water from source 692 in reservoir 672 if desired. An additional purification or treatment component in the form of a filter or ultraviolet bactericidal light 674 can be added to dialysis recirculation fluid circuit 614 as illustrated or alternatively to blood or patient circuit 612. In the latter instance, when added to blood or patient circuit 612, fluid exiting dialyzer 620 via flow path 624 can be further filtered or subject to a bactericidal light to enhance the bacterial purity of system 610. The treated fluid can then enter individual 616 via flow path 624.

System 610 may further include one or more conductivity sensor. Conductivity sensors may be placed at any suitable location along the fluid flow pathway to confirm that salt ions have been desirably removed or added as the case may be. For example, and referring to the particular embodiment shown in FIG. 9, a conductivity sensor 696a can be in fluid connection between EDI component 690 and ion exchange unit 660, such that the conductivity of the fluid (and therefore the ion content of the fluid) exiting the EDI component 690 can be determined. Alternatively or additionally, a conductivity sensor 696b can be in fluid connection between ion exchange unit 690 and dialysate reservoir 672 (when present) or dialyzer 620. When dialysate reservoir 672 is present, a conductivity sensor 696c may be in fluid connection between dialysate reservoir 672 and dialyzer 620. In some embodiments, the circuit 614 includes at least two conductivity sensors 696a, 696b, and 696c. Thus in some embodiments, recirculation circuit 614 includes all three of conductivity sensors 696a, 696b and 696c.

System 610 further includes one or more fluid pump for transporting spent dialysate, regenerated dialysate, reagent concentrates, water, or other fluids throughout the circuit. Each and every pump construction and positioning specification and alternative discussed above for system 510 is applicable to system 610. In FIG. 9, pumps 698a to 698f are used to transport various fluids. In embodiments in which pump dialysate reservoir 672 is used to hold regenerated dialysate, pump 698a feeds the regenerated dialysate from reservoir to dialyzer 620. Reservoir 672 is alternatively a filter, such as an ultrafilter. Or, the filter can be provided in addition to reservoir 672. In either case, the filter, e.g., ultrafilter, may bring the water or dialysis fluid close to or to injectable quality level. Ultrapure or sterile water is provided from sterile or ultrapure water source 692 to dialysate reservoir 672 via pump 698b and to EDI component 690 via pump 698f. Pump 698f pumps tap water from tap 699 to EDI unit 690. Acid concentrate and bicarbonate are provided from concentrate or fluid metering source 648 by pump 698c and/or 698d. Acid solution from acid source 694 is provided to EDI component 690 via pump 698e. Pumps 698a to 698f can be of any type described above and can be used if desired with a dialysis pumping cassette.

In addition to the modifications described herein, the dialysis fluid recycling systems can be further enhanced in several ways. First, the dialysis fluid recycling systems can remove nearly all solutes from the used or spent dialysis solution (including therapeutically beneficial solutes, which would then need to be re-added). The dialysis fluid recycling systems can also be designed to allow reduced removal of the active osmotic agent in the peritoneal dialysis fluid (e.g., glucose or dextrose). The osmotic reagent can be replaced with a longer acting molecule, such as glucose microspheres that can be reintroduced into the dialysis fluid, to maintain the osmotic gradient in the individual.

Figure 17B:
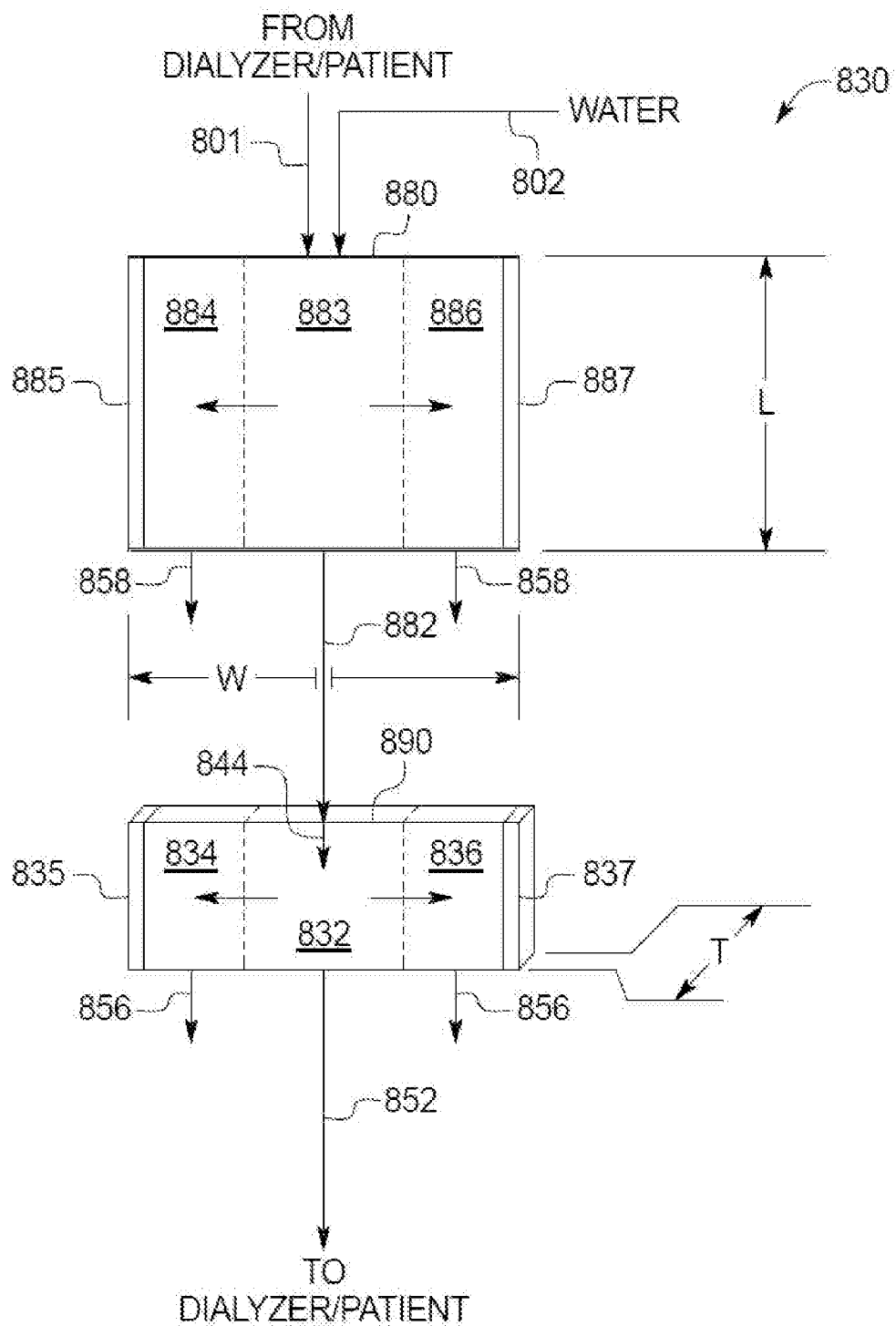
FIG. 17B is a schematic of a combination ED/EDI unit according to another embodiment of the present disclosure.

Apparatuses 730 and 830 of FIGS. 17A and 17B can be used in any type of blood dialysis treatment, e.g., hemodialysis ("HD"), hemofiltration ("HF"), or hemodiafiltration ("HDF"). Apparatuses 730 and 830 can also be used in any type of peritoneal dialysis ("PD") treatment, such as continuous cycling peritoneal dialysis ("CCPD") or tidal peritoneal dialysis. A combination ED/EDI apparatus is prepared by modifying a commercially available ED unit (e.g., ED200, PCCell) to reduce the width W by half and double the separation length L, and by modifying a single EDI unit (e.g., EDI15, Millipore) to reduce the thickness by half. FIG. 17A shows a combination ED/EDI apparatus 730 that is capable of removing 99.9% of ions when a 180 millimolar ("mM") spent dialysate stream is processed at 250 mL/min. The system 730 includes a single ED unit 780 in the illustrated embodiment, which is in fluid communication with a plurality (e.g., two, three, four or more) of EDI units 790. ED unit 780 includes a central chamber 783, a cation chamber 786 having a cathode 787, and an anion chamber 784 having an anode 785. Each EDI unit 790 includes a central chamber 732, a cation chamber 736 having a cathode 737, and an anion chamber 734 having an anode 735. Each EDI unit 790 rejects a cation waste stream from the cation chamber 736 and an anion waste stream from the anion chamber 734, which can be routed to drain 790.

In the configuration shown in FIG. 17A, the EDI units 790 (e.g., each model EDI15, Millipore) are connected in parallel to one ED unit 780 (e.g., ED200, PCCell). In an example operation, a spent dialysate stream enters ED unit 780 via fluid path 701 at a flow rate of for example 250 mL/min. When operated at typical power levels (e.g, 130 watts), the treated fluid stream exiting ED unit 780 via flow path 782 has about 70% lower ion content than the spent dialysis stream (i.e., ED unit 780 removes about 70% of the ions from the spent dialysate stream). This partially treated fluid stream is then split and fed into three EDI units 790, each operating at a typical power level of about forty watts. The treated streams exiting the EDI units 790 are combined in fluid path 752, which has about 0.1% of the ion content of the original spent dialysate fluid stream (i.e., the combination ED unit 780 with the three EDI units 790 operating in parallel each at about forty watts removes about 99.9% of the ions remaining from the original spent dialysis stream). The total power consumption in this example is 130+40+40+40=250 watts, and the total ion removal is about 99.9%.

FIG. 17B shows another ED/EDI embodiment of the present disclosure. In comparison to apparatus 730 shown in FIG. 17A, apparatus 830 uses only a single modified EDI unit 890 which, in combination with a single modified ED unit 880, is capable of removing at least about 99.9% of the ions from a 180 mM spent dialysate stream at a flow rate of 250 mL/min, and uses significantly less power (about 170 watts vs. about 250 watts).

In the embodiment shown in FIG. 17B, spent dialysate enters the modified ED unit 880 via fluid paths 801 and 802, respectively. The modified ED unit 880 has in one embodiment about twice the separation length L as ED unit 780 shown in FIG. 17A, and includes central chamber 883, a cation chamber 886 having a cation 887, and an anion chamber 884 having an anode 885. The extended separation length L can be accomplished by any suitable method including, for example and without limitation, inclusion of additional flow channels (e.g., one or more flow barriers in the housing of the modified ED unit 880) that forces the spent dialysate to travel farther through the modified ED unit 880 before exiting compared to a comparable, unmodified ED unit having a standard flow path length L. In one embodiment, modified ED unit 880 has an extended separation length L while having the same or essentially the same exterior dimensions as a comparable unmodified ED unit.

Due to the extended separation length L, modified ED unit 880 can achieve the same or better ion removal performance than commercially available ED unit 780 (e.g., at least about 85%, at least about 88%, or at least about 90%, etc., of the ions in the spent dialysate stream), while requiring less power input. For example, modified ED unit 880 can be operated at about 90% to 95%, e.g., about 92%, of its standard power level (e.g., at about 120 watts compared to PCCell ED200's standard power level of 130 watts). The resulting partially treated fluid stream exits the modified ED unit 880 via fluid path 882 and enters the modified EDI unit 890, where it flows through central chamber 832 via flow path 844.

Modified EDI unit 890 has a reduced thickness T compared to EDI unit 790. The reduced thickness T can achieved by any suitable method including, for example, reducing the distance between membrane layers within the EDI unit. In one embodiment, modified EDI unit 890 has reduced distance between membrane layers while having the same or essentially the same external dimensions as a comparable unmodified EDI unit.

Modified EDI unit 890 includes a central chamber 832, a cation chamber 836 having a cathode 837, and an anion chamber 834 having an anode 835. In one embodiment, modified EDI unit 890 is operated at an elevated power level compared to EDI unit 790 (e.g., about 105% to about 150%, or about 120% to 130%, or more particularly about 125% (about 50 watts) compared to Millipore's EDI15 power rating of 40 watts), such that the ED unit 880 and EDI unit 890 collectively remove at least about 99%, or at least about 99.2%, or more particularly at least about 99.5%, or most particularly about 99.9%, of the ions in the spent dialysate stream.

In an example operation, blood or spent dialysate enters modified ED unit 880 via flow path 801. Fluid streams 858 exiting cation chamber 886 and anion chamber 884 can be routed to drain (not shown) or recycled through the ED/EDI unit 830 in the same manner as shown in FIGS. 8 and 9. Fluid stream 882 exits the central chamber 883 of modified ED unit 880 and enters central chamber 832 of modified EDI unit 890 along flow path 844. Fluid streams 856 exiting cation chamber 836 and anion chamber 834 can be routed to drain (not shown) or recycled through the ED/EDI unit 830 in the same manner as shown in FIGS. 8 and 9. Purified blood or dialysate exits modified EDI unit 890 via flow path 852 and is returned to the patient or dialyzer.

Combination ED/EDI unit 830 shown in FIG. 17B uses fewer EDI units (which are comparatively more expensive than ED units) and consumes less power than required by the comparable combination ED/EDI system or apparatus 730 shown in FIG. 17A. Thus, for a given flow rate, the cost and total power consumption of the combination modified ED unit/modified EDI apparatus 830 of the present disclosure are reduced, while achieving the same ion removal performance as apparatus 730 and other presently available ED units and EDI units. Comparative power consumption data required to achieve a total ion removal of 99.9% is provided in Tables 1A and 1B:

TABLE 1A

Power Consumption for Unmodified ED Unit with Three Unmodified EDI Units.

| Entry | Dialysate Input solute conc. | flow rate (mL/min) | ED Unit (1) Power | % Ion Removal | EDI Units (3) Power | % Ion Removal | Total Power |
|---|---|---|---|---|---|---|---|
| 1A | 140 mM | 100 | 35 W | 86% | 22 W | 99.3% | 57 W |
| 2A | 180 mM | 250 | 102 W | 78% | 66 W | 99.5% | 168 W |

TABLE 1B

Power Consumption for Modified ED Unit with One Modified EDI Unit.

| Entry | Dialysate Input solute conc. | flow rate (mL/min) | Mod. ED Unit (1) Power | % Ion Removal | Mod. EDI Units (1) Power | % Ion Removal | Total Power |
|---|---|---|---|---|---|---|---|
| 1B | 140 mM | 100 | 38 W | 94% | 1 W | 98.4% | 39 W |
| 2B | 180 mM | 250 | 115 W | 88% | 49 W | 99.2% | 164 W |

Apparatuses 730 and 830 can be used with any of the systems discussed above, such as systems 10, 110, 210, 310, 410, 510, and/or 610.

EXAMPLES

By way of example and not limitation, the following examples are illustrative of embodiments of the present disclosure.

Example 1

Experiments to determine the extent of the electrolyte removal using an EDI unit were performed. The experiments simulated EDI treatment of a post-urease dialysate. A peritoneal dialysis solution was spiked with 3200 ppm of Ammonium Carbonate (2000 ppm of urea can be converted into 3200 ppm of ammonium carbonate by urease). In different studies, the dialysis solution was passed through the EDI unit at a flow rate of 100 mL/min and 200 mL/min.

A Millipore EDI-15 Cell with a PK Precision VSP-12010 DC power supply was used as the EDI unit. Conductivity of the dialysis solution was measured using an Amber Science EC3084 Conductivity Meter.

Figure 6:
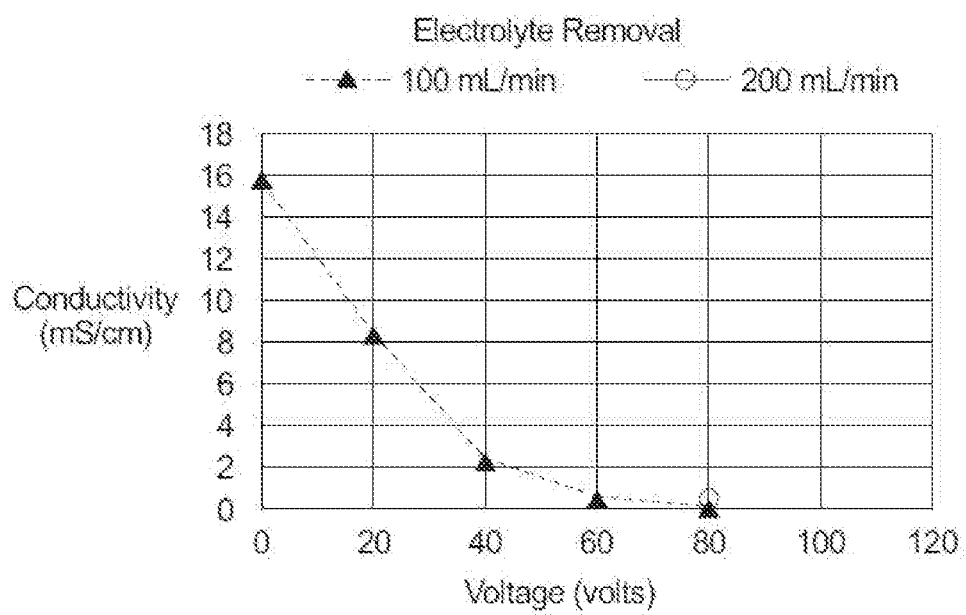
FIG. 6 is a graph showing the conductivity of a dialysis solution treated using an EDI unit versus the operating voltage of the EDI unit.
Figure 7:
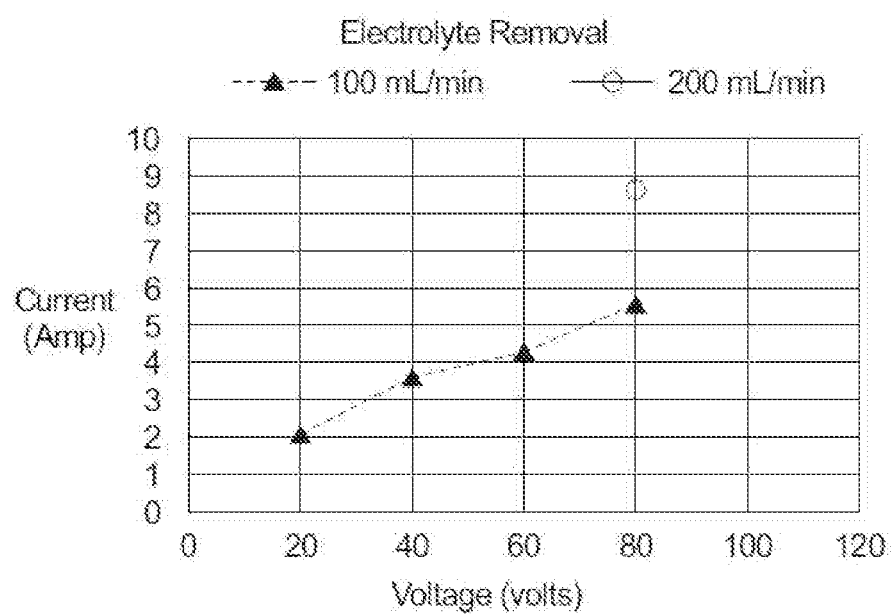
FIG. 7 is a graph showing the operating current of an EDI unit versus the operating voltage of the EDI unit.

During the experiments, the conductivity of the treated dialysis solution versus corresponding voltage/current of the EDI unit was measured. The final conductivity was compared to the original conductivity of the untreated dialysis solution. A summary of the results is shown in Table 2 and FIGS. 6 and 7. FIG. 6 shows the conductivity of a dialysis solution treated using the EDI unit versus the operating voltage of the EDI unit. FIG. 7 shows the operating current of the EDI unit versus the operating voltage of the EDI unit.

TABLE 2

| Dialysate flow rate (mL/min) | Voltage (Volts) | Current (Ampere) | Conductivity (mS/cm) | % Removal |
|---|---|---|---|---|
| 100 | 0 | 0 | 15.9 | 0 |
| 100 | 20 | 2.1 | 8.4 | 47 |
| 100 | 40 | 3.6 | 2.28 | 86 |
| 100 | 60 | 4.3 | 0.48 | 97 |
| 100 | 80 | 5.6 | 0.08 | 99 |
| 200 | 80 | 8.6 | 0.44 | 97 |

As shown in Table 2 and FIGS. 6 and 7, a 99% electrolyte removal from the dialysis solution can be achieved using the EDI unit. It was also found that the EDI unit can be operated at a reduced voltage and reduced current to allow a specific percentage of electrolytes to pass through. This could allow the use of a smaller size EDI unit for better portability. In this case, the small amount of residue electrolytes, including ammonium ions, can be removed by a supplemental ion-exchange resin column down stream from the EDI unit.

Example 2

Figure 10:
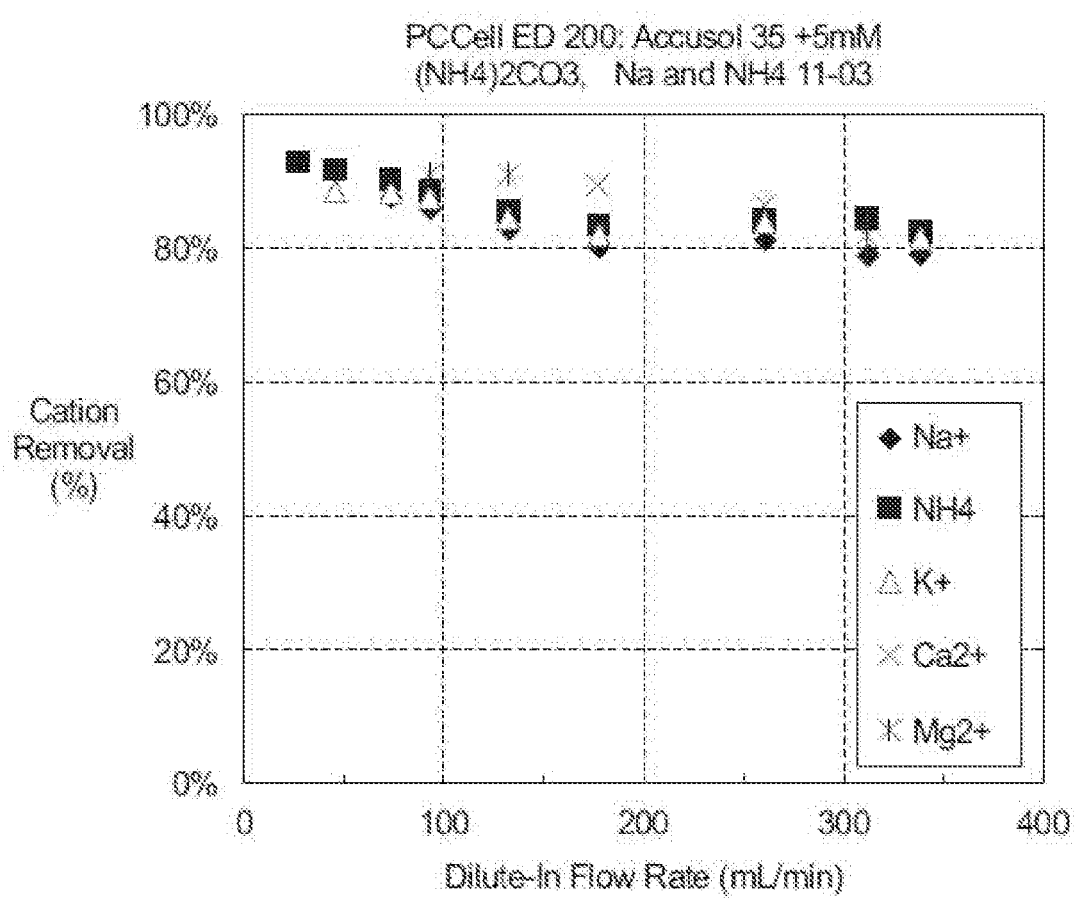
FIG. 10 is a graph showing removal of sodium, ammonium, potassium, calcium and magnesium cations as a function of flow rate for a dialysis fluid treated using an ED/EDI combination unit in one embodiment of the present disclosure.

Experiments to determine the extent of the electrolyte removal using an ED unit of the present disclosure were performed. The experiments simulated ED treatment of a post-urease dialysate. A peritoneal dialysis solution (Accusol 35, Baxter Healthcare) was spiked with Ammonium Carbonate (5 mM) and passed through the ED unit at 45 volts and at a flow rate of about twenty to about 340 mL/min. The electrolyte concentration was analyzed using an Olympus AU400e Clinical Analyzer. The percentage of each ion removed was determined by comparing it with the concentration of the solution entering the EDI unit. Cation removal preference as a function of dilute-in flow rate is shown in FIG. 10 for sodium, ammonium, potassium, calcium and magnesium. In general, the ED/EDI unit preferentially removed magnesium over calcium over sodium over potassium over ammonium cations under these conditions. Anion removal preference as a function of dilute-in flow rate for the same system is shown in FIG. 11 for bicarbonate and chloride anions, with chloride being removed more preferentially than bicarbonate.

Figure 11:
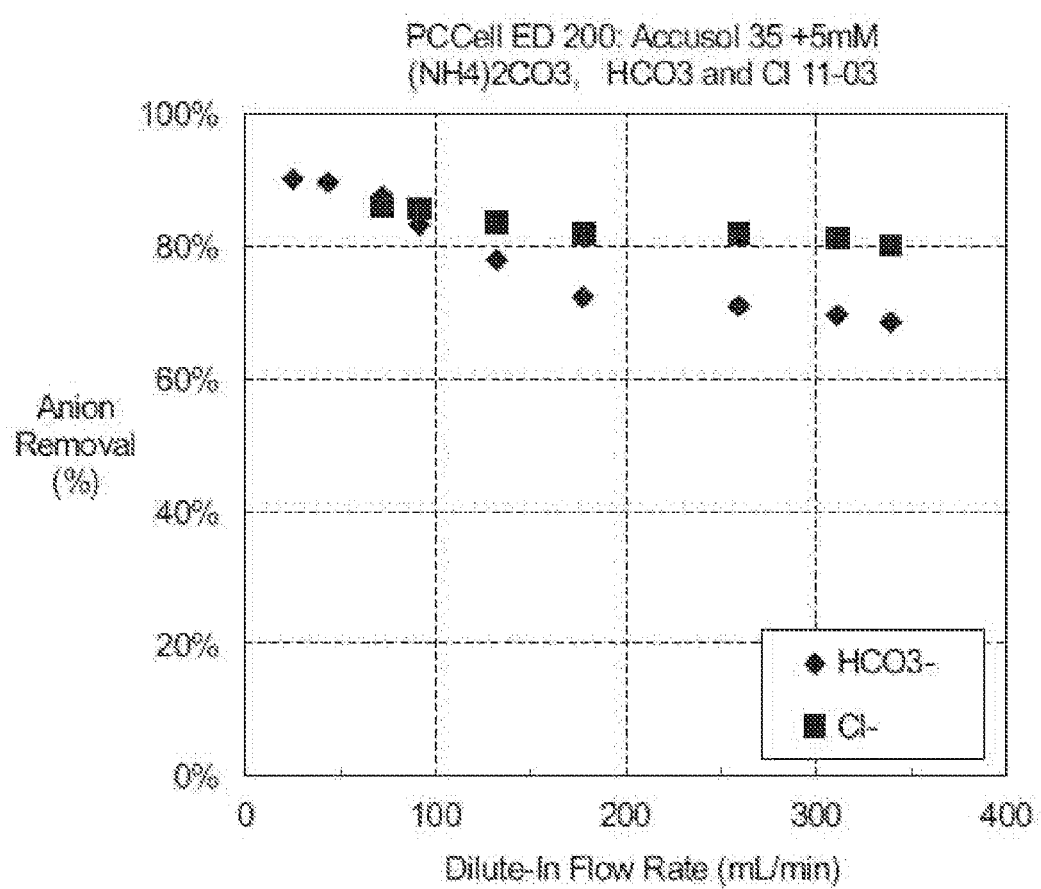
FIG. 11 is a graph showing removal of hypochlorite and chloride anions as a function of flow rate for a dialysis fluid treated using an ED component of an ED/EDI unit in one embodiment of the present disclosure.
Figure 12:
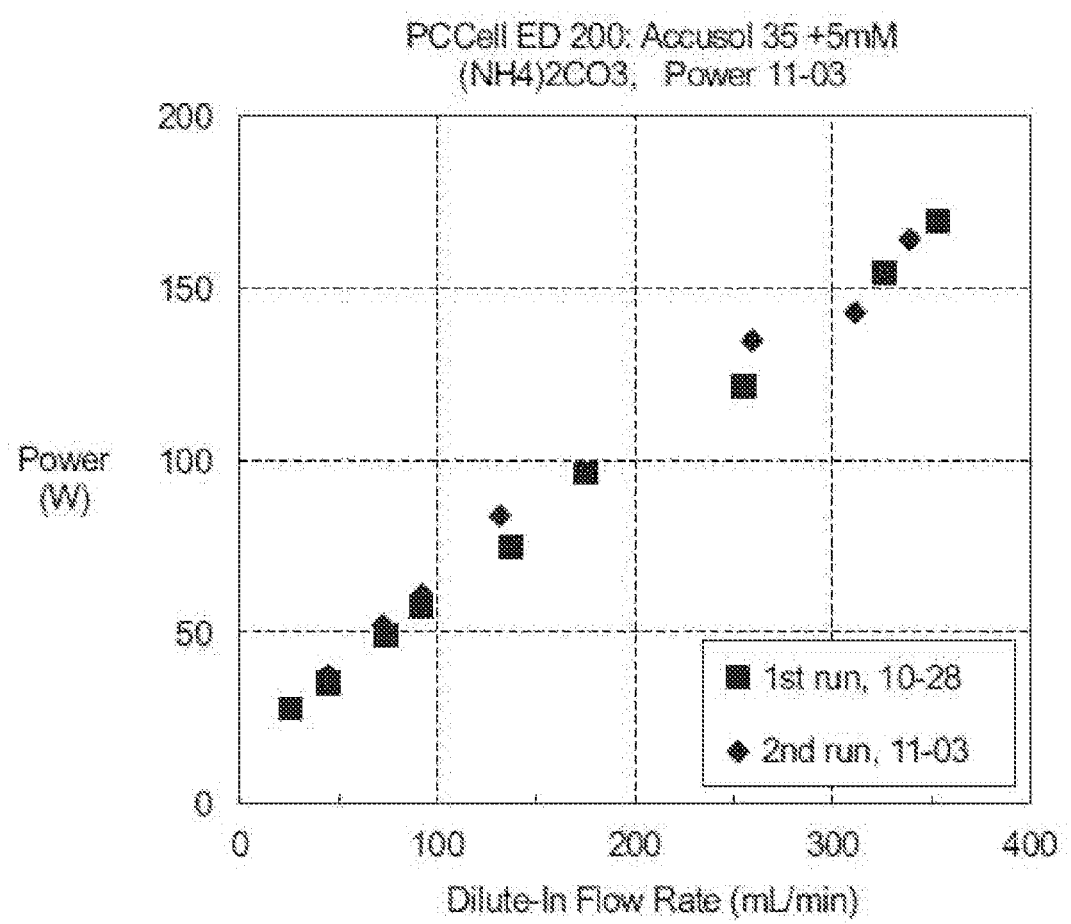
FIG. 12 is a graph showing power consumption versus the flow rate for an ED component of an ED/EDI unit in one embodiment of the present disclosure.

The corresponding power consumption of the EDI unit at these data points on shown on FIG. 10 and FIG. 11 is plotted in FIG. 12. As shown in FIG. 12, less than 150 watts is required to remove greater than 80% of the ammonium cations at a dialysate flow rate of less than 300 mL/min.

Example 3

Experiments to determine the extent of the electrolyte removal using an EDI unit were performed. The experiments simulated EDI treatment of a post-urease dialysate. A peritoneal dialysis solution (Accusol 35, Baxter Healthcare) was passed through the EDI unit at flow rates of eighty-nine mL/min and forty-seven mL/min. The electrolyte concentration was analyzed using an Olympus AU400e Clinical Analyzer. The percentage of each ion removed was determined by comparing it with the concentration of the solution entering the EDI unit.

Figure 13:
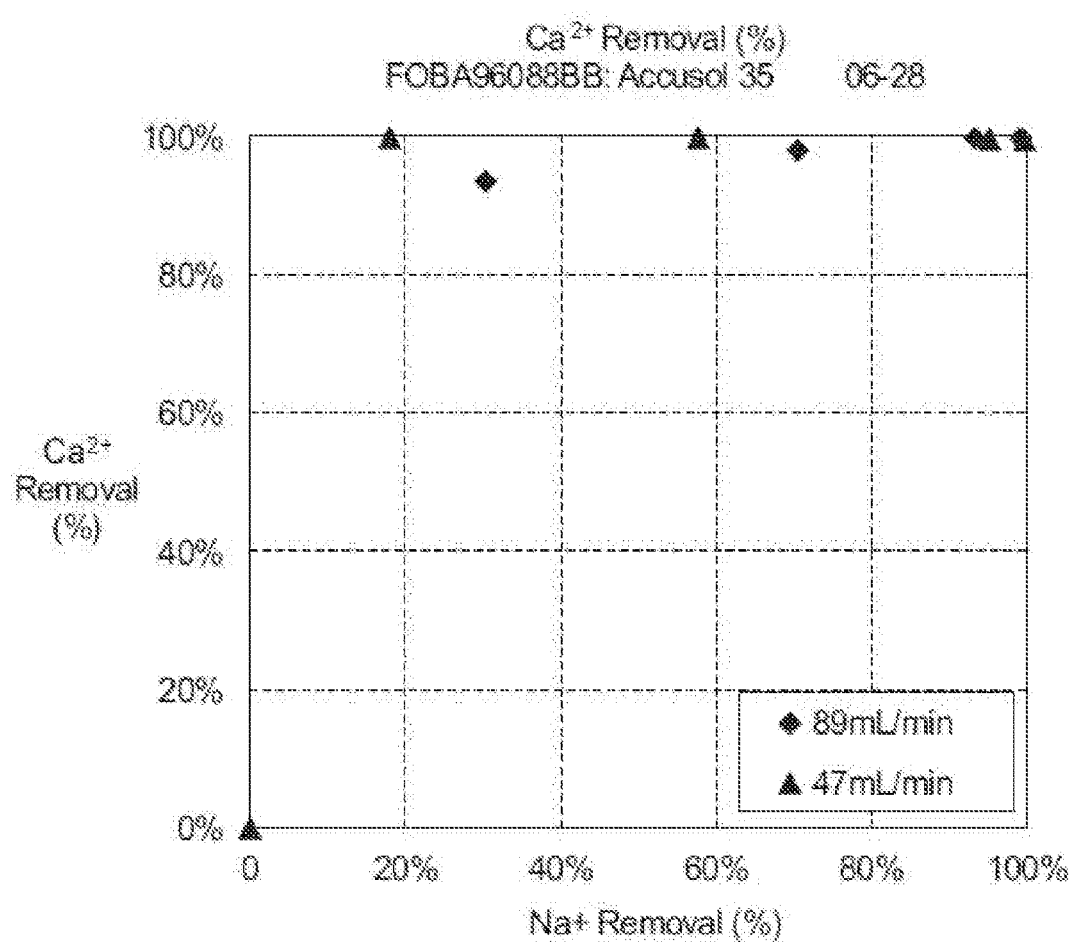
FIG. 13 is a graph showing removal of calcium versus sodium cations at two flow rates using an EDI component of an ED/EDI unit according to one embodiment of the present disclosure.

FIG. 13 shows relative removal rates for calcium compared to sodium. At both forty-seven and eighty-nine mL/min flow rates, calcium cations were removed at a faster rate than sodium cations were removed. For example, at forty-seven mL/min, less than 20% of the sodium cations had been removed by the time the calcium cations were nearly completely removed from the dialysate solution. Results were qualitatively similar at a flow rate of eighty-nine mL/min. This data indicates that EDI preferentially removes calcium cations over sodium cations.

Figure 14:
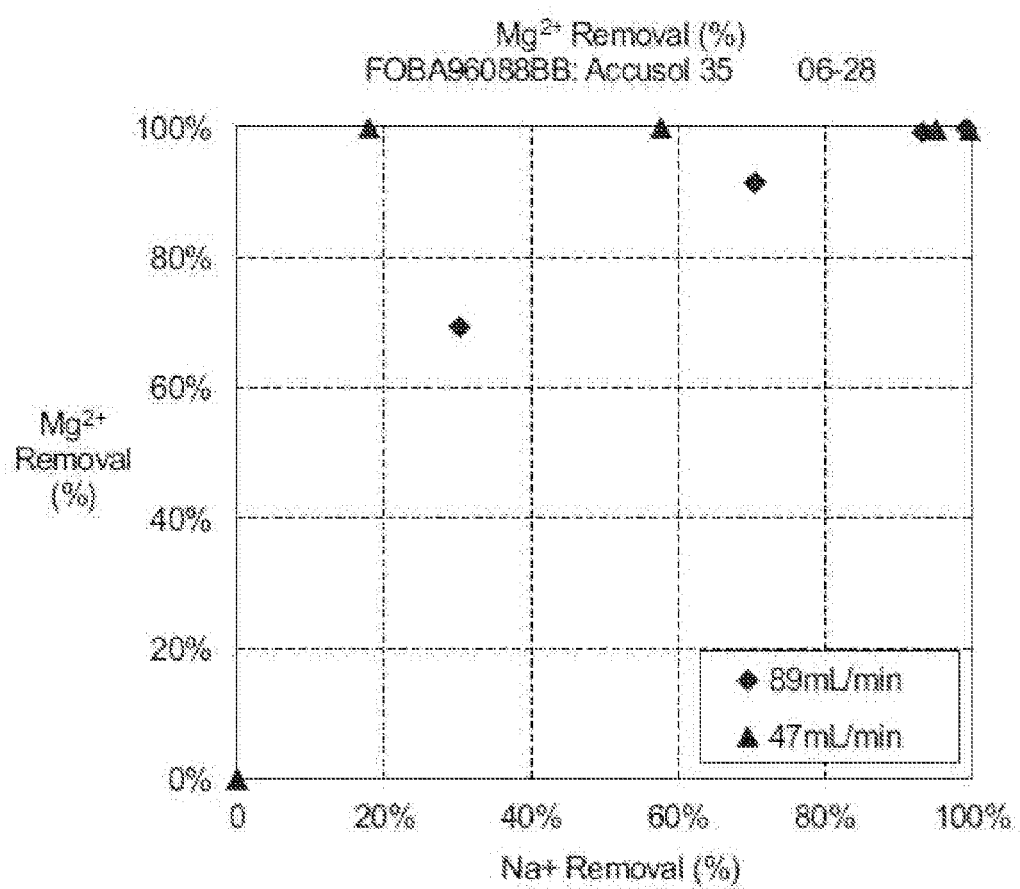
FIG. 14 is a graph showing removal of magnesium versus sodium cations at two flow rates using an EDI component of an ED/EDI unit according to one embodiment of the present disclosure.

FIG. 14 shows relative removal rates for magnesium and sodium cations at forty-seven and eighty-nine mL/min. At both forty-seven and eighty-nine mL/min flow rates, magnesium cations were removed at a faster rate than sodium cations were removed. For example, at forty-seven mL/min, less than 20% of the sodium cations had been removed by the time the magnesium cations were nearly completely removed from the dialysate solution. Results were qualitatively similar at a flow rate of eighty-nine mL/min. This data indicates that EDI preferentially removes magnesium cations over sodium cations.

Example 4

Experiments to determine the extent of the electrolyte removal using an EDI unit were performed. The experiments simulated EDI treatment of a post-urease dialysate. A peritoneal dialysis solution having 140 Mm sodium chloride and thirty Mm ammonium carbonate was prepared (an initial molar ratio of $Na^+/NH_4^+$ of about 2.3:1 was passed through the EDI unit at flow rates of one-hundred mL/min and ninety-seven mL/min under different applied electric current conditions to achieve different levels of ion removal by the EDI unit. The electrolyte concentrations of the fluid entering the EDI unit and the effluent fluid from the EDI unit were analyzed using an Olympus AU400e Clinical Analyzer. The molar ratio of $Na^+/NH_4^+$ in the effluent fluid from the EDI unit is compared with the molar ratio of $Na^+/NH_4^+$ in the incoming fluid. An increase of the $Na^+/NH_4^+$ molar ratio will indicate a preference of removing $NH_4^+$ ion over $Na^+$ by the EDI unit.

Figure 15:
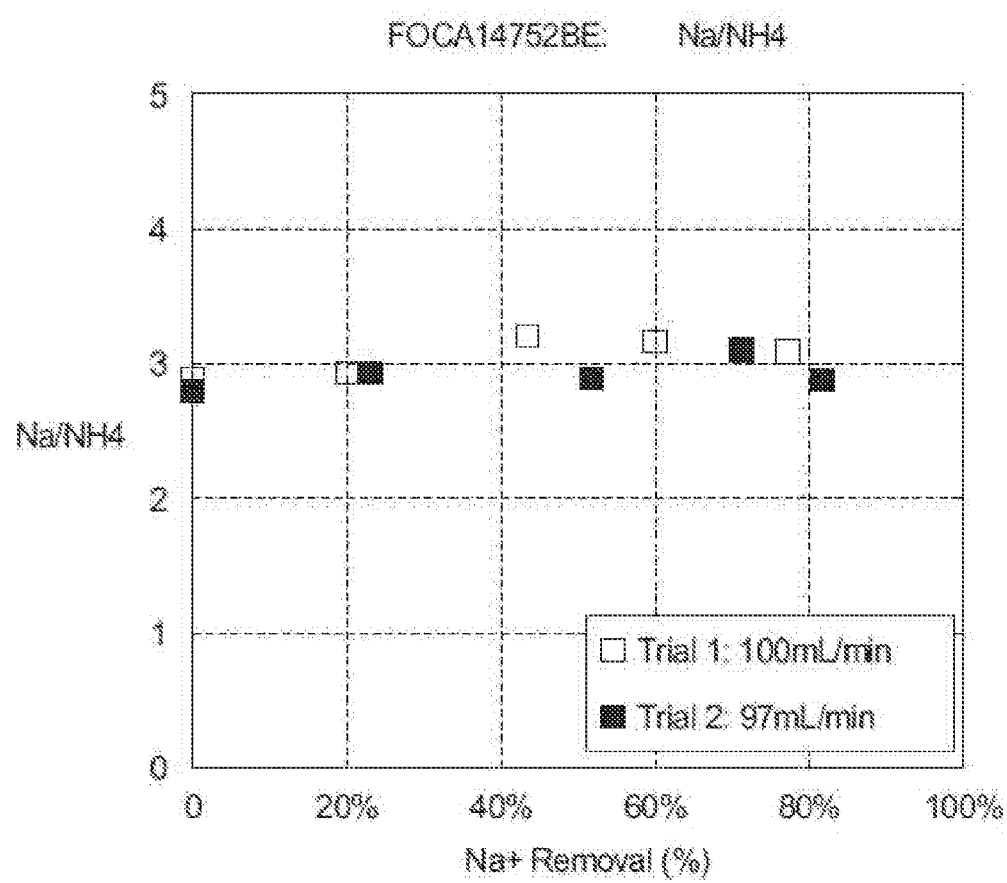
FIG. 15 is a graph showing the ratio of sodium to ammonium removed versus percentage of sodium cations removed at two flow rates using an EDI component of an ED/EDI unit according to one embodiment of the present disclosure.

FIG. 15 shows the relative removal rates for sodium and ammonium cations at different levels of ion removal. In this experiment, the simulated dialysate was passed through the EDI unit at flow rates of one-hundred mL/min and ninety-seven mL/min. At each flow rate and across the range of different ion removal, the sodium/ammonium molar ratio increased slightly over the incoming fluid, indicating that the EDI removed slightly more ammonium cations than sodium ions at both flow rates.

Figure 16:
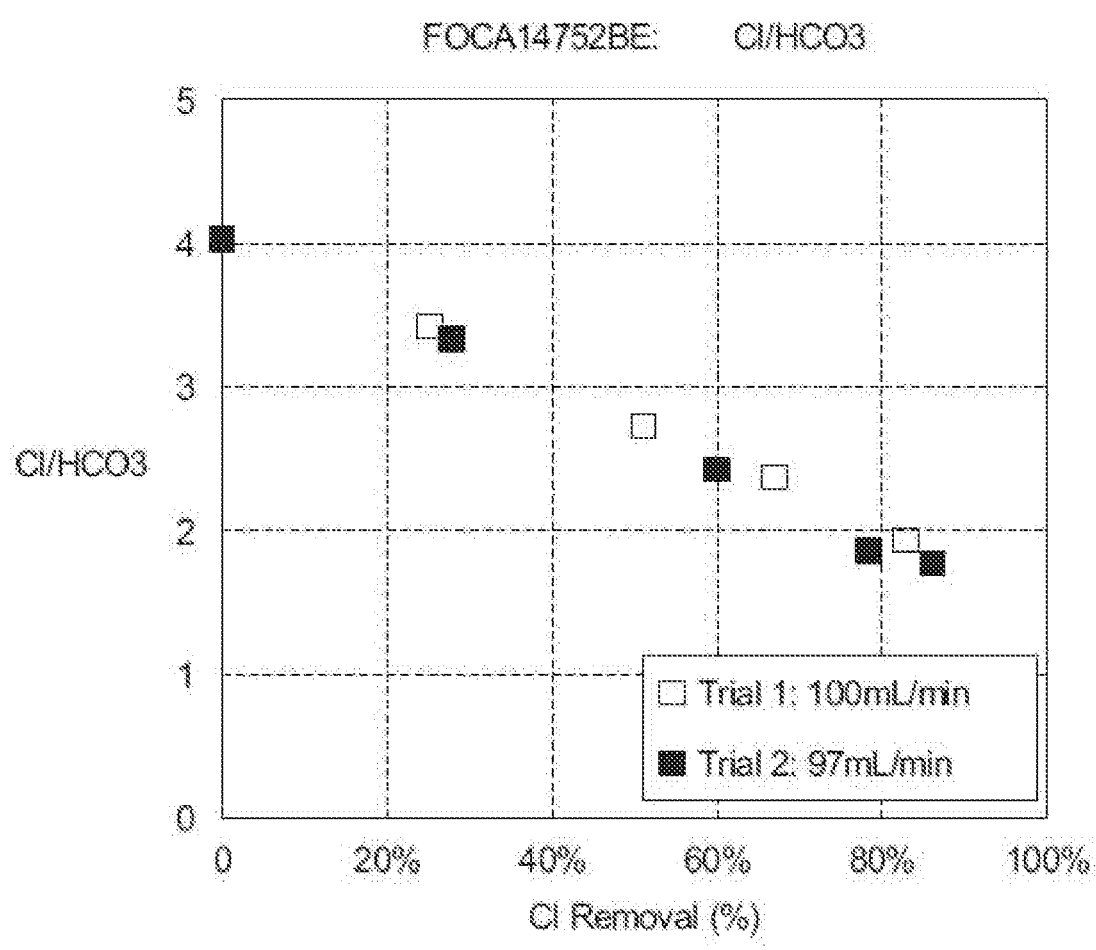
FIG. 16 is a graph showing the ratio of chloride to hypochlorite removed versus percent of chloride anions removed at two flow rates using an EDI component of an ED/EDI unit according to one embodiment of the present disclosure.

FIG. 16 shows relative removal rates for chloride and bicarbonate anions when the same dialysate solution used to generate FIG. 15 was passed through the EDI unit at flow rates of one-hundred mL/min and ninety-seven mL/min. The initial $Cl^-/HCO_3^-$ ratio was about 4.7:1 in the incoming fluid, and decreased over the range of different levels of ion removal and at both flow rates. A decrease of the $Cl^-/HCO_3^-$ molar ratio in the effluent fluid in comparison with the incoming fluid will indicate a preference of removing $Cl^-$ ion over $HCO_3^-$ by the EDI unit. This data indicates that EDI removes chloride anions at a faster rate than bicarbonate anions.

Aspects of the Present Disclosure

Aspects of the subject matter described herein may be useful alone or in combination one or more other aspect described herein. Without limiting the foregoing description, in a first aspect of the present disclosure, a dialysis fluid system recycling used dialysis fluid comprises a carbon source, a urease source in fluid communication with the carbon source, and an electrodialysis/electrodionization ("ED/EDI") unit in fluid communication with at least one of the carbon and urease sources, the ED/EDI unit including an ED component, and an EDI component in fluid communication with the ED component.

In accordance with a second aspect of the present disclosure, which may be used with any one or more aspect discussed herein, the dialysis fluid system includes an ion exchange unit operating with the ED/EDI unit to recycle used dialysis fluid.

In accordance with a third aspect of the present disclosure, which may be used with any one or more aspect discussed herein, the dialysis fluid system includes a concentrate metering source located downstream of the ED/EDI unit.

In accordance with a fourth aspect of the present disclosure, which may be used with any one or more aspect discussed herein, at least a portion of fluid within the ED/EDI unit of the dialysis fluid system is recirculated back into the ED/EDI unit.

In accordance with a fifth aspect of the present disclosure, which may be used with any one or more aspect discussed herein, the ED unit includes multiple ED units.

In accordance with a sixth aspect of the present disclosure, which may be used with any one or more aspect discussed herein, a hemodialysis system recycling used dialysis fluid comprises a blood circuit and a dialysis fluid circuit in fluid communication with a dialyzer, a carbon source in the dialysis fluid circuit, a urease source in fluid communication with the carbon source, and an electrodialysis/electrodionization ("ED/EDI") unit in fluid communication with at least one of the carbon and urease sources and, the ED/EDI unit including an ED component and an EDI component in fluid communication with the ED component.

In accordance with a seventh aspect of the present disclosure, which may be used with any one or more aspect discussed herein, the hemodialysis system includes an ion exchange unit in the dialysis fluid circuit.

In accordance with an eighth aspect of the present disclosure, which may be used with any one or more aspect discussed herein, the hemodialysis system includes a concentrate metering source located downstream of the ED/EDI unit.

In accordance with a ninth aspect of the present disclosure, which may be used with any one or more aspect discussed herein, the hemodialysis system includes a filter in the dialysis fluid circuit.

In accordance with a tenth aspect of the present disclosure, which may be used with any one or more aspect discussed herein, the hemodialysis system includes an ultraviolet bactericidal light positioned and arranged to irradiate at least a portion of the blood circuit or the dialysis fluid circuit.

In accordance with an eleventh aspect of the present disclosure, which may be used with any one or more aspect discussed herein, a peritoneal dialysis system comprises a dialysis fluid recirculation flow path configured to be placed in fluid communication with the peritoneal cavity of a patient, a carbon source in the dialysis fluid recirculation flow path, a urease source in fluid communication with the carbon source, and an electrodialyzer/electrodeionization ("ED/EDI") unit in fluid communication with one of the carbon and urease sources, the ED/EDI unit including an ED component, and an EDI component in fluid communication with the ED component.

In accordance with a twelfth aspect of the present disclosure, which may be used with any one or more aspect discussed herein, the peritoneal dialysis system includes an ion exchange unit in the dialysis fluid recirculation flow path.

In accordance with a thirteenth aspect of the present disclosure, which may be used with any one or more aspect discussed herein, the peritoneal dialysis system includes a concentrate metering source located downstream of the ED/EDI unit.

In accordance with a fourteenth aspect of the present disclosure, which may be used with any one or more aspect discussed herein, the dialysis fluid recirculation flow path of the peritoneal dialysis system runs from the patient or a dialyzer, through the carbon source, the urease source and the ED/EDI unit, in any order, back to the patient or the dialyzer.

In accordance with a fifteenth aspect of the present disclosure, which may be used with any one or more aspect discussed herein, the peritoneal dialysis system includes an ultraviolet bactericidal light positioned and arranged to irradiate at least a portion of the dialysis fluid recirculation flow path.

In accordance with a sixteenth aspect of the present disclosure, which may be used with any one or more aspect discussed herein, a method of performing hemodialysis comprises passing dialysis fluid from a dialyzer through, in any order, a carbon source, a urease source, an electrodialysis ("ED") component, and an electrodeonization ("EDI") component to produce a cleaned dialysis fluid, and returning the cleaned dialysis fluid to the dialyzer.

In accordance with a seventeenth aspect of the present disclosure, which may be used with any one or more aspect discussed herein, the method includes passing the dialysis fluid through an ion exchange unit before returning the cleaned dialysis fluid to the dialyzer.

In accordance with an eighteenth aspect of the present disclosure, which may be used with any one or more aspect discussed herein, the method includes adding at least one dialysis fluid concentrate to the dialysis fluid before returning the cleaned dialysis fluid to the dialyzer.

In accordance with a nineteenth aspect of the present disclosure, which may be used with any one or more aspect discussed herein, the method includes draining a portion of the dialysis fluid that is passed through at least one of the ED and EDI components.

In accordance with a twentieth aspect of the present disclosure, which may be used with any one or more aspect discussed herein, the method includes recirculating a portion of the dialysis fluid that is passed through at least one of the ED and EDI components.

In accordance with a twenty-first aspect of the present disclosure, which may be used with any one or more aspect discussed herein, the method includes adding at least one of sterile/injectable or tap water to the dialysis fluid.

In accordance with a twenty-second aspect of the present disclosure, which may be used with any one or more aspect discussed herein, the method includes filtering the dialysis fluid before returning the cleaned dialysis fluid to the dialyzer.

In accordance with a twenty-third aspect of the present disclosure, which may be used with any one or more aspect discussed herein, a method of performing peritoneal dialysis comprises recirculating dialysis fluid removed from a patient or dialysate through, in any order, a carbon source, a urease source, an electrodialysis ("ED") component, and an electrodeionization ("EDI") component to produce a cleaned dialysis fluid, and returning the cleaned dialysis fluid to the patient or dialyzer.

In accordance with a twenty-fourth aspect of the present disclosure, which may be used with any one or more aspect discussed herein, the method includes passing the dialysis fluid through an ion exchange unit before returning the cleaned dialysis fluid to the patient.

In accordance with a twenty-fifth aspect of the present disclosure, which may be used with any one or more aspect discussed herein, the method includes adding at least one dialysis fluid concentrate to the dialysis fluid before returning the cleaned dialysis fluid to the patient.

In accordance with a twenty-sixth aspect of the present disclosure, any of the structure, functionality and alternatives illustrated and described in connection with any combination of one, or more, or all of FIGS. 1 to 17B may be used in combination with any one, or more, or all of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis fluid system recycling used dialysis fluid, the system comprising:
   a carbon source;
   a urease source in fluid communication with the carbon source; and
   an electrodialysis/electrodeionization ("ED/EDI") unit in fluid communication with at least one of the carbon and urease sources, the ED/EDI unit including
   (i) an ED component, and
   (ii) an EDI component in fluid communication with the ED component, wherein the ED component and the EDI component are separate.

2. The dialysis fluid system of claim 1, which includes an ion exchange unit operating with the ED/EDI unit to recycle used dialysis fluid.

3. The dialysis fluid recycling system of claim 1, which includes a concentrate metering source located downstream of the ED/EDI unit.

4. The dialysis fluid recycling system of claim 1, wherein at least a portion of fluid within the ED/EDI unit is recirculated back into the ED/EDI unit.

5. The dialysis fluid recycling system of claim 1, wherein the ED unit includes multiple ED units.

6. A hemodialysis system recycling used dialysis fluid, the hemodialysis system comprising:
   a blood circuit and a dialysis fluid circuit in fluid communication with a dialyzer;
   a carbon source in the dialysis fluid circuit;
   a urease source in fluid communication with the carbon source; and
   an electrodialysis/electrodeionization ("ED/EDI") unit in fluid communication with at least one of the carbon and urease sources and, the ED/EDI unit including an ED component and an EDI component in fluid communication with the ED component, wherein the ED component and the EDI component are separate.

7. The hemodialysis system of claim 6, which includes an ion exchange unit in the dialysis fluid circuit.

8. The hemodialysis system of claim 6, which includes a concentrate metering source located downstream of the ED/EDI unit.

9. The hemodialysis system of claim 6, which includes a filter in the dialysis fluid circuit.

10. The hemodialysis system of claim 6, which includes an ultraviolet bactericidal light positioned and arranged to irradiate at least a portion of the blood circuit or the dialysis fluid circuit.

11. A peritoneal dialysis system comprising:
    a dialysis fluid recirculation flow path configured to be placed in fluid communication with the peritoneal cavity of a patient;
    a carbon source in the dialysis fluid recirculation flow path;
    a urease source in fluid communication with the carbon source; and
    an electrodialyzer/electrodeionization ("ED/EDI") unit in fluid communication with one of the carbon and urease sources, the ED/EDI unit including
    (i) an ED component, and
    (ii) an EDI component in fluid communication with the ED component, wherein the ED component and the EDI component are separate.

12. The peritoneal dialysis system of claim 11, which includes an ion exchange unit in the dialysis fluid recirculation flow path.

13. The peritoneal dialysis system of claim 11, which includes a concentrate metering source located downstream of the ED/EDI unit.

14. The peritoneal dialysis system of claim 11, wherein the dialysis fluid recirculation flow path runs from the patient or a dialyzer, through the carbon source, the urease source and the ED/EDI unit, in any order, back to the patient or the dialyzer.

15. The peritoneal dialysis system of claim 11, which includes an ultraviolet bactericidal light positioned and arranged to irradiate at least a portion of the dialysis fluid recirculation flow path.

* * * * *